(12) United States Patent
Patangay et al.

(10) Patent No.: US 8,048,001 B2
(45) Date of Patent: Nov. 1, 2011

(54) METHOD AND APPARATUS FOR DETECTING ATRIAL FILLING PRESSURE

(75) Inventors: Abhilash Patangay, Little Canada, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1261 days.

(21) Appl. No.: 11/558,967

(22) Filed: Nov. 13, 2006

(65) Prior Publication Data

US 2007/0066913 A1    Mar. 22, 2007

Related U.S. Application Data

(63) Continuation-in-part of application No. 10/334,694, filed on Dec. 30, 2002.

(51) Int. Cl.
*A61B 5/0225* (2006.01)
*A61B 5/021* (2006.01)

(52) U.S. Cl. ....................................................... 600/528

(58) Field of Classification Search .................... 607/23; 600/508, 514, 528, 485
See application file for complete search history.

(56) References Cited

U.S. PATENT DOCUMENTS

| | | | |
|---|---|---|---|
| 3,965,339 A * | 6/1976 | Mount et al. ................. | 600/485 |
| 4,446,872 A | 5/1984 | Marsoner et al. | |
| 4,548,204 A | 10/1985 | Groch et al. | |
| 4,586,514 A | 5/1986 | Schlager et al. | |
| 4,899,751 A * | 2/1990 | Cohen ............................ | 607/23 |
| 5,010,889 A * | 4/1991 | Bredesen et al. ............. | 600/528 |
| 5,417,717 A * | 5/1995 | Salo et al. ........................ | 607/18 |
| 5,685,317 A | 11/1997 | Sjostrom | |
| 5,687,738 A | 11/1997 | Shapiro et al. | |
| 5,697,375 A | 12/1997 | Hickey | |
| 5,792,195 A | 8/1998 | Carlson et al. | |
| 5,836,987 A | 11/1998 | Baumann et al. | |
| 5,860,933 A | 1/1999 | Don Michael | |
| 5,935,081 A | 8/1999 | Kadhiresan | |

(Continued)

FOREIGN PATENT DOCUMENTS

JP            61-202653            9/1986

(Continued)

OTHER PUBLICATIONS

Bulgrin, J. R., et al., "Comparison of Short-Time Fourier, Wavelet and Time-Domain Analyses of Intracardiac Sounds", *Biomedical Sciences Instrumentation*, 29, (1993), 465-472.

(Continued)

*Primary Examiner* — Niketa Patel
*Assistant Examiner* — Joseph Stoklosa
(74) *Attorney, Agent, or Firm* — Schwegman, Lundberg & Woessner, P.A.

(57) ABSTRACT

A cardiac rhythm management system provides for ambulatory monitoring of hemodynamic performance based on quantitative measurements of heart sound related parameters for diagnostic and therapeutic purposes. Monitoring of such heart sound related parameters allows the cardiac rhythm management system to determine a need for delivering a therapy and/or therapy parameter adjustments based on conditions of a heart. This monitoring also allows a physician to observe or assess the hemodynamic performance for diagnosing and making therapeutic decisions. Because the conditions of the heart may fluctuate and may deteriorate significantly between physician visits, the ambulatory monitoring, performed on a continuous or periodic basis, ensures a prompt response by the cardiac rhythm management system that may save a life, prevent hospitalization, or prevent further deterioration of the heart.

20 Claims, 13 Drawing Sheets

U.S. PATENT DOCUMENTS

| | | | |
|---|---|---|---|
| 6,026,324 A | 2/2000 | Carlson | |
| 6,045,513 A | 4/2000 | Stone et al. | |
| 6,058,329 A | 5/2000 | Salo et al. | |
| 6,298,269 B1 | 10/2001 | Sweeney | |
| 6,366,811 B1 | 4/2002 | Carlson | |
| 6,368,283 B1 | 4/2002 | Xu et al. | |
| 6,527,729 B1 | 3/2003 | Turcott | |
| 6,626,842 B2 | 9/2003 | Oka | |
| 6,643,548 B1* | 11/2003 | Mai et al. | 607/17 |
| 6,650,940 B1 | 11/2003 | Zhu et al. | |
| 6,792,308 B2 | 9/2004 | Corbucci | |
| 6,845,263 B2 | 1/2005 | Kawaguchi | |
| 6,869,404 B2 | 3/2005 | Schulhauser et al. | |
| 7,113,825 B2 | 9/2006 | Pastore et al. | |
| 7,115,096 B2 | 10/2006 | Siejko et al. | |
| 7,404,802 B2* | 7/2008 | Siejko et al. | 600/528 |
| 2002/0072684 A1 | 6/2002 | Stearns | |
| 2002/0151938 A1 | 10/2002 | Corbucci | |
| 2003/0069608 A1 | 4/2003 | Sweeney | |
| 2003/0093002 A1 | 5/2003 | Kuo | |
| 2003/0208240 A1 | 11/2003 | Pastore et al. | |
| 2004/0106960 A1 | 6/2004 | Siejko et al. | |
| 2004/0122297 A1 | 6/2004 | Stahmann et al. | |
| 2004/0122484 A1 | 6/2004 | Hatlestad et al. | |
| 2004/0127792 A1 | 7/2004 | Siejko et al. | |
| 2004/0138572 A1 | 7/2004 | Thiagarajan | |
| 2004/0167417 A1 | 8/2004 | Schulhauser et al. | |
| 2004/0215264 A1 | 10/2004 | Van Bentem | |
| 2004/0267148 A1 | 12/2004 | Arand et al. | |
| 2005/0102001 A1 | 5/2005 | Maile et al. | |
| 2005/0148896 A1 | 7/2005 | Siejko et al. | |
| 2005/0149136 A1 | 7/2005 | Siejko et al. | |
| 2005/0222515 A1* | 10/2005 | Polyshchuk et al. | 600/528 |
| 2005/0288721 A1 | 12/2005 | Girouard et al. | |
| 2006/0020294 A1 | 1/2006 | Brockway et al. | |
| 2006/0155204 A1 | 7/2006 | Wariar et al. | |
| 2006/0161070 A1 | 7/2006 | Siejko et al. | |

FOREIGN PATENT DOCUMENTS

| | | |
|---|---|---|
| JP | 63-109103 U | 7/1988 |
| JP | 63-290544 | 11/1988 |
| JP | 03015441 | 1/1991 |
| JP | 06-277189 | 10/1994 |
| JP | 2000-060846 | 2/2000 |
| JP | 2000-316825 | 11/2000 |
| JP | 2001145606 | 5/2001 |
| WO | WO-0122885 A1 | 4/2001 |
| WO | WO-0156651 A1 | 8/2001 |
| WO | WO-2004/060483 A1 | 7/2004 |
| WO | WO-2005122902 A1 | 12/2005 |
| WO | WO-2006078757 A1 | 7/2006 |

OTHER PUBLICATIONS

Leatham, A., "Splitting of the First and Second Heart Sounds", *Lancet*, 267 (6839), (Sep. 25, 1954), 607-614.

Marcus, G. M., et al., "Association Between Phonocardiographic Third and Fourth Heart Sounds and Objective Measures of Left Ventricular Function", *JAMA*, 293(18), (May 11, 2005), 2238-2244.

Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s,(1992), 856-862.

Siejko, Krzysztof Z., et al., "A Third Heart Sound Activity Index for Heart Failure Monitoring", U.S. Appl. No. 11/465,878, filed Aug. 21, 2006, 35 Pages.

Siejko, Krzysztof Z., et al., "Physiological Event Detection Systems and Methods", U.S. Appl. No. 11/276,735, filed Mar. 12, 2006, 56 Pages.

Weissler, Arnold M., et al., "Beside technics for the Evaluation of Ventricular Function in Man", *The American Journal of Cardiology*, vol. 23, (Apr. 1965), 577-583.

Weissler, Arnold M., et al., "Systolic Time Intervals in Heart Failure in Man", *Circulation*, vol. XXXVII, No. 2, (Feb. 1968), 149-159.

Wood, J. C., et al., "Time-Frequency Transforms: A New Approach to First Heart Sound Frequency Dynamics", *IEEE Transactions on Biomedical Engineering*, 39 (7), IEEE Service Center, US,(Jul. 1, 1992), 730-740.

Zhang, Y., et al., "Ischemia Detection Using a Heart Sound Sensor", U.S. Appl. No. 11/148,107, filed Jun. 8, 2005, 41 pgs.

"U.S. Appl. No. 10/334,694, Final Office Action mailed Nov. 27, 2009", 13 pgs.

"U.S. Appl. No. 10/334,694, Response filed Dec. 8, 2008 to Final Office Action mailed Oct. 7, 2008", 18 pgs.

"U.S. Appl. No. 10/334,694, Response filed Jun. 19, 2008 to Non-Final Office Action mailed Mar. 19, 2008", 20 pgs.

"U.S. Appl. No. 10/334,694, Advisory Action mailed Dec. 23, 2008", 3 pgs.

"U.S. Appl. No. 10/334,694, Non-Final Office Action mailed Mar. 19, 2008", 15 pgs.

"U.S. Appl. No. 10/334,694, Response filed Jul. 20, 2007 to Non-Final Office Action mailed Apr. 20, 2007", 18 pgs.

"U.S. Appl. No. 10/334,694, Advisory Action mailed Dec. 18, 2007", 3 pgs.

"U.S. Appl. No. 10/334,694, Final Office Action mailed Oct. 1, 2007", 13 pgs.

"U.S. Appl. No. 10/334,694, Final Office Action mailed Oct. 7, 2008", 14 pgs.

"U.S. Appl. No. 10/334,694, Non-Final Office Action Apr. 20, 2007", 12 pgs.

"U.S. Appl. No. 10/334,694, Non-Final Office Action Nov. 27, 2006", 9 pgs.

"U.S. Appl. No. 10/334,694, Non-Final Office Action mailed Mar. 18, 2009", 14 pgs.

"U.S. Appl. No. 10/334,694, Response filed Feb. 27, 2007 to Non-Final Office Action mailed Nov. 27, 2006", 20 pgs.

"U.S. Appl. No. 10/334,694, Response filed Mar. 1, 2010 to Final Office Action mailed Nov. 27, 2009", 21 pgs.

"U.S. Appl. No. 10/334,694, Response filed Jul. 17, 2009 to Non Final Office Action mailed Mar. 18, 2009", 18 pgs.

"U.S. Appl. No. 10/334,694, Response filed Dec. 3, 2007 to Final Office Action mailed Oct. 1, 2007", 21 pgs.

"European Application Serial No. 03800278.8, Communication dated Oct. 17, 2007", 4 pgs.

"European Application Serial No. 03800278.8, Response filed Feb. 18, 2008 to Communication dated Oct. 17, 2007", 14 pgs.

"International Application Serial No. PCT/US03/41481, International Search Report mailed Jun. 4, 2004", 7 pgs.

"Japanese Application Serial No. 2004-565783, Office Action mailed Mar. 11, 2010", 2 pgs.

"Japanese Application Serial No. 2004-565783, Office Action mailed Nov. 11, 2009", 2 pgs.

"Japanese Application Serial No. 2004-565783, Amendment and Argument filed Feb. 5, 2010 to Office Action Mailed Nov. 11, 2009", (w/ English Translation of Amended Claims), 14 pgs.

"U.S. Appl. No. 10/334,694, Non-Final Office Action mailed Apr. 30, 2010", 13 pgs.

"U.S. Appl. No. 10/334,694, Response filed Jul. 27, 2010 to Non Final Office Action mailed Apr. 30, 2010", 19 pgs.

"Japanese Application Serial No. 2004-565783, Notice of Allowance mailed Aug. 9, 2010".

* cited by examiner

METHOD AND APPARATUS FOR DETECTING ATRIAL FILLING PRESSURE

CROSS-REFERENCE TO RELATED APPLICATION

This application is a continuation-in-part of commonly assigned Siejko et al. U.S. patent application Ser. No. 10/334,694, entitled "METHOD AND APPARATUS FOR MONITORING OF DIASTOLIC HEMODYNAMICS," filed Dec. 30, 2002, which is hereby incorporated by reference.

TECHNICAL FIELD

This document relates generally to cardiac rhythm management systems and particularly, but not by way of limitation, to such a system sensing heart sounds for monitoring, diagnosis, and therapy control.

BACKGROUND

A heart is the center of a person's circulatory system. It includes a complex electromechanical system performing two major pumping functions. The left portions of the heart, including the left atrium and the left ventricle, draw oxygenated blood from the lungs and pump it to the organs of the body to provide the organs with their metabolic needs for oxygen. The right portions of the heart, including the right atrium and the right ventricle, draw deoxygenated blood from the organs and pump it into the lungs where the blood gets oxygenated. These mechanical pumping functions are accomplished by contractions of the myocardium (heart muscles). In a normal heart, the sinus node, the heart's natural pacemaker, generates electrical signals, called action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently. Thus, the normal pumping functions of the heart, indicated by hemodynamic performance, require a normal electrical system to generate the action potentials and deliver them to designated portions of the myocardium with proper timing, a normal myocardium capable of contracting with sufficient strength, and a normal electromechanical association such that all regions of the heart are excitable by the action potentials.

The function of the electrical system is indicated by electrocardiography (ECG) with at least two electrodes placed in or about the heart to sense the action potentials. When the heart beats irregularly or otherwise abnormally, one or more ECG signals indicate that contractions at various cardiac regions are chaotic and unsynchronized. Such conditions are known as cardiac arrhythmias. Cardiac arrhythmias result in a reduced pumping efficiency of the heart, and hence, diminished blood circulation. Examples of such arrhythmias include bradyarrhythmias, that is, hearts that beat too slowly or irregularly, and tachyarrhythmias, that is, hearts that beat too quickly. A patient may also suffer from weakened contraction strength related to deterioration of the myocardium. This further reduces the pumping efficiency. For example, a heart failure patient suffers from an abnormal electrical conduction system with excessive conduction delays and deteriorated heart muscles that result in asynchronous and weak heart contractions, and hence, reduced pumping efficiency, or poor hemodynarnic performance. Thus, in addition to ECG, the function of the mechanical system and the electromechanical association need to be measured to assess the overall pumping performance of the heart.

Characteristics of heart sounds are known to be indicative of various mechanical properties and activities of the heart. Measurements performed with synchronously recorded ECG and heart sounds provide for quantitative indications of the electromechanical association. For example, amplitudes of the third heart sound (S3) and fourth heart sound (S4) are related to filing pressures of the left ventricle during diastole. Fundamental frequencies of S3 and S4 are related to ventricular stiffness and dimension. Chronic changes in S3 amplitude is correlated to left ventricular chamber stiffness and degree of restrictive filling. Change in the interval between atrial contraction and S4 is correlated to the changes in left ventricular end diastolic pressure. Such parameters, being correlated to the heart's mechanical properties and electromechanical association, quantitatively indicate abnormal cardiac conditions, including degrees of severity, and need of appropriate therapies.

For these and other reasons, there is a need for a system providing for cardiac therapy based on parameters related to heart sounds.

OVERVIEW

A system provides for ambulatory monitoring of hemodynamic performance based on quantitative measurements of heart sound related parameters for diagnostic and therapeutic purposes. Monitoring of such heart sound related parameters allows the system to determine a need for delivering a therapy and/or therapy parameter adjustments based on conditions of a heart. This monitoring also allows a physician to observe or assess the hemodynamic performance for diagnosing and making therapeutic decisions. The monitoring can also be used to trigger an alert to notify a patient or a caregiver. Because the conditions of the heart may fluctuate and may deteriorate significantly between physician visits, the ambulatory monitoring, performed on a continuous or periodic basis, ensures a prompt response by the system that may save a life, prevent hospitalization, or prevent further deterioration of the heart.

In one embodiment, a system includes an acoustic senor, a cardiac sensing circuit, a heart sound detector, a parameter generator, a processor, and a therapy circuit. The acoustic sensor senses an acoustic energy and produces an acoustic sensor signal indicative heart sounds. The cardiac sensing circuit senses a cardiac signal indicative of cardiac electrical events. The heart sound detector detects selected heart sounds based on the acoustic sensor signal and the cardiac signal. The parameter generator generates values of at least one predetermined parameter related to the selected heart sounds. The processor includes a trending analyzer that produces and analyzes at least one trend related to the selected heart sounds based on the values of the predetermined parameter. The therapy circuit delivers cardiac therapy with at least one therapy parameter determined based on the trend.

In another embodiment, an acoustic energy is sensed to produce an acoustic sensor signal indicative heart sounds. One or more cardiac signals indicative of cardiac electrical events are also sensed. Selected heart sounds are detected. Parameter values related to the selected heart sounds and selected cardiac electrical events are generated. Selected parameter values, which are associated with one or more types of the selected heart sounds, are analyzed to produce at least one trend. A therapy, with at least one parameter determined based on the trend, is delivered.

In yet another embodiment, a system includes an implantable device. The implantable device includes an acoustic sensor, a cardiac sensing circuit, a gating module, a heart sound detector, a measurement module, and a therapy circuit. The acoustic sensor senses an acoustic energy to produce an acoustic sensor signal indicative heart sounds. The cardiac sensing circuit senses at least one cardiac signal indicative of cardiac electrical events. The gating module generates heart sound detection windows each timed for detection of one of selected heart sounds based on a time of occurrence of one of selected cardiac electrical events. The heart sound detector detects the selected heart sounds. The measurement module generates parameter values related to the selected heart sounds. The therapy circuit delivers a therapy based on the parameter values.

In Example 1, a system includes an implantable medical device. The implantable medical device includes a heart sound sensor, configured to sense a heart sound signal of a heart. The system also includes a heart sound detector, coupled to the heart sound sensor, the heart sound detector configured to detect at least one parameter indicative of an atrial filling pressure of the heart using the heart sound signal. The system also includes a processor, coupled to the heart sound detector, the processor configured to compare the at least one parameter to a threshold.

In Example 2, the atrial filling pressure of Example 1 optionally includes a left atrial filling pressure.

In Example 3, the at least one parameter of Examples 1-2 optionally includes at least one measurement, feature, characteristic, computation, or interval of the heart sound signal. In Example 4, the at least one measurement, feature, characteristic, computation, or interval of the heart sound signal of Examples 1-3 optionally includes at least one of an amplitude of a third heart sound (S3), a split second heart sound (S2) time interval, an S2-S3 time interval, and a normalized amplitude or interval of at least one measurement, feature, or characteristic of the heart sound signal.

In Example 5, the implantable medical device of Examples 1-4 optionally includes a cardiac sensor, coupled to the heart sound detector, the cardiac sensor configured to sense a cardiac signal of the heart. The heart sound detector of Examples 1-4 is also optionally configured to detect the at least one parameter using the heart sound signal and the cardiac signal.

In Example 6, the at least one parameter of Examples 1-5 optionally includes at least one measurement, feature, characteristic, computation, or interval between at least one cardiac signal feature and at least one heart sound signal feature.

In Example 7, the at least one parameter of Examples 1-6 optionally includes a systolic time interval (STI).

In Example 8, the threshold of Examples 1-7 optionally includes a predefined threshold.

In Example 9, the threshold of Examples 1-8 optionally includes an absolute threshold.

In Example 10, the system of Examples 1-9 optionally includes a posture sensor, coupled to the processor, the posture sensor configured to sense a posture signal. The processor of Examples 1-9 is also optionally configured to compare the at least one parameter to the threshold using the posture signal.

In Example 11, the system of Examples 1-10 optionally includes an alert module, coupled to the processor, the alert module configured to generate an alert using the at least one parameter.

In Example 12, the alert of Examples 1-11 is optionally configured to be generated with a predefined specificity.

In Example 13, the alert of Examples 1-12 is optionally configured to be generated with a predefined specificity equal to or greater than 85%.

In Example 14, the alert of Examples 1-13 is optionally configured to be generated with a predefined specificity equal to or greater than 90%.

In Example 15, a system includes means for sensing a heart sound signal of a heart using an implanted heart sound sensor, such as by using a heart sound sensor to sense the heart sound signal of the heart. The system also includes means for detecting at least one parameter indicative of an atrial filling pressure of the heart using the heart sound signal, such as by using a heart sound detector to detect at least one parameter indicative of an atrial filling pressure of the heart using the heart sound signal. The system also includes means for comparing the at least one parameter to a threshold, such as by using a processor to compare the at least one parameter to the threshold.

In Example 16, a method includes sensing a heart sound signal of a heart using an implanted heart sound sensor. The method also includes detecting at least one parameter indicative of an atrial filling pressure of the heart using the heart sound signal. The method also includes comparing the at least one parameter to a threshold.

In Example 17, the method of Example 16 optionally includes detecting the at least one parameter indicative of an atrial filling pressure includes detecting at least one parameter indicative of a left atrial filling pressure.

In Example 18, the method of Examples 16-17 optionally includes detecting the at least one parameter includes detecting at least one measurement, feature, characteristic, computation, or interval of the heart sound signal.

In Example 19, the method of Examples 16-18 optionally includes detecting the at least one measurement, feature, characteristic, computation, or interval of the heart sound signal includes detecting at least one of an amplitude of a third heart sound (S3), a split second heart sound (S2) time interval, an S2-S3 time interval, and a normalized amplitude or interval of at least one measurement, feature, or characteristic of the heart sound signal.

In Example 20, the method of Examples 16-19 optionally includes sensing a cardiac signal of the heart using an implanted cardiac sensor. The detecting the at least one parameter of Examples 16-19 also optionally includes using the heart sound signal and the cardiac signal.

In Example 21, the detecting the at least one parameter of Examples 16-20 optionally includes detecting at least one measurement, feature, characteristic, computation, or interval between at least one cardiac signal feature and at least one heart sound signal feature.

In Example 22, the detecting the at least one parameter of Examples 16-21 optionally includes detecting at least one systolic time interval (STI).

In Example 23, the comparing the at least one parameter to a threshold of Examples 16-22 optionally includes comparing the at least one parameter to a predefined threshold.

In Example 24, the comparing the at least one parameter to a threshold of Examples 16-23 optionally includes comparing the at least one parameter to an absolute threshold.

In Example 25, the method of Examples 16-24 optionally includes sensing a posture signal using a posture sensor. The comparing the at least one parameter to a threshold of Examples 16-24 also optionally includes using the posture signal.

In Example 26, the method of Examples 16-25 optionally includes generating an alert using the at least one parameter.

In Example 27, the generating an alert of Examples 16-26 optionally includes generating an alert with a predefined specificity.

In Example 28, the generating an alert with a predefined specificity of Examples 16-27 optionally includes generating an alert with a predefined specificity of at least 85%.

In Example 29, the generating an alert with a predefined specificity of Examples 16-28 optionally includes generating an alert with a predefined specificity of at least 90%.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
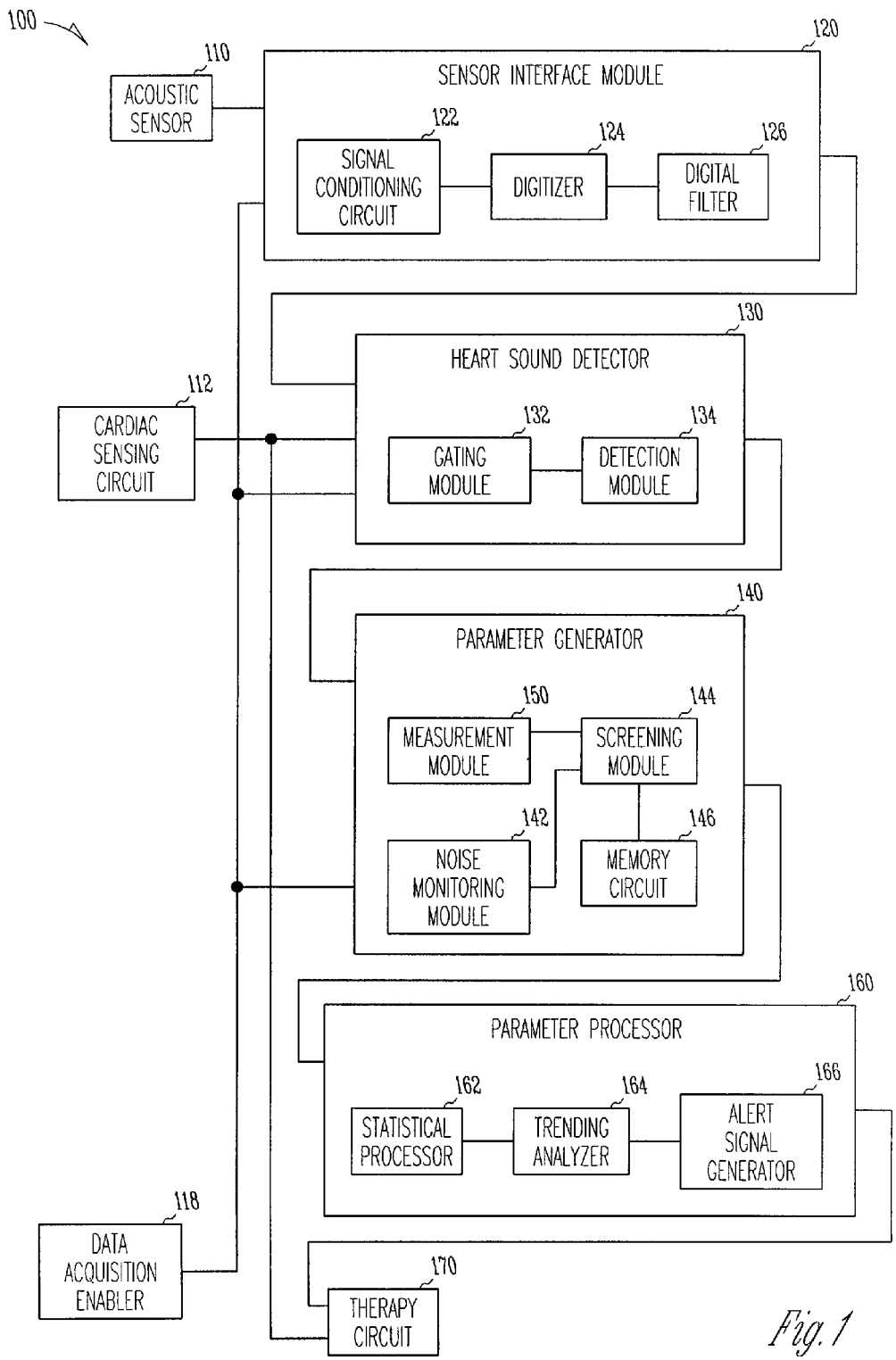
FIG. 1 is a block diagram illustrating an embodiment of a heart-sound based hemodynamics monitoring and therapy control system.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

This document discusses, among other things, a system monitoring heart sounds indicative of a heart's mechanical events related to the heart's pumping functions and hemodynamic performance to allow, among other things, diagnosis of cardiac conditions and selection of therapies treating the cardiac conditions. The cardiac rhythm management systems include systems having, for example, pacemakers, cardioverter/defibrillators, pacemaker/defibrillators, and cardiac resynchronization therapy (CRT) devices. One specific example of a cardiac rhythm management system that monitors and analyses heart sounds is described in co-pending, commonly assigned Siejko et al. U.S. patent application Ser. No. 10/307,896, entitled "PHONOCARDIOGRAPHIC IMAGE-BASED ATRIOVENTRICULAR DELAY OPTIMIZATION," filed Dec. 2, 2002, which is hereby incorporated by reference in its entirety. However, it is to be understood that the present methods and apparatuses may be employed in other types of medical devices, including, but not being limited to, drug delivery systems and various types of cardiac monitoring devices.

Known and studied heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

Throughout this document, "heart sound" includes audible and inaudible mechanical vibrations caused by cardiac activity that can be sensed with an accelerometer. Accordingly, the scope of "acoustic energy" in this document extends to energies associated with such mechanical vibrations.

Throughout this document, "user" refers to a physician or other caregiver who examines and/or treats a patient using one or more of the methods and apparatuses reported in the present document. Unless noted otherwise, S1, S2, S3, and S4 refer to the first, second, third, and fourth heart sounds, respectively, as a heart sound type, or as one or more occurrences of the corresponding type heart sounds, depending on the context.

FIG. 1 is a block diagram illustrating an embodiment of a heart-sound based hemodynamics monitoring and therapy control system 100. System 100 includes, among other things, an acoustic sensor 110, a sensor interface module 120, a cardiac sensing circuit 112, a heart sound detector 130, a parameter generator 140, a data acquisition timer 118, a parameter processor 160, and a therapy circuit 170. In one embodiment, system 100 is a totally implantable system adapted to be implanted into a patient. In an alternative embodiment, system 100 is an external system that does not include any implantable component. In another alternative embodiment, system 100 includes both implantable and external components.

Acoustic sensor 110 senses an acoustic energy or mechanical vibration energy related to cardiac mechanical activities and converts the acoustic energy to an acoustic sensor signal indicative of heart sounds. The acoustic sensor signal is an electrical signal indicative of timing, strength, and frequency characteristics related to the heart sounds. Acoustic sensor 110 is disposed in a heart, or near the heart in a location where the acoustic energy related to the cardiac mechanical activities can be sensed. In one embodiment, acoustic sensor 110 includes an accelerometer disposed in or near a heart. In another embodiment, acoustic sensor 110 includes a microphone disposed in or near a heart.

Sensor interface module 120 has a signal input connected to the output of acoustic sensor 110 to receive the acoustic sensor signal. It processes the acoustic sensor signal to prepare for detection of selected type heart sounds. The selected type heart sounds are heart sounds selected for a purpose of monitoring a patient's hemodynamic performance indicated by the measurable characteristics of these heart sounds. In one specific embodiment, the selected type heart sounds includes S3 and S4, which are indicative of ventricular diastolic hemodynamic performance. Sensor interface module includes a signal conditioning circuit 122, a digitizer 124, and a digital filter 126. Signal conditioning circuit 122 receives the acoustic sensor signal as an analog signal from acoustic sensor 110, and performs initial conditioning of the acoustic sensor signal. In one embodiment, signal conditioning circuit 122 improves the signal-to-noise ratio of the acoustic sensor signal. It includes an amplifier and a filter to amplify the acoustic sensor signal while reducing the noise therein. In one embodiment, the filter is an analog filter that substantially reduces amplitudes of noises that are not within the frequency spectrum of the selected type heart sounds. In another embodiment, the filter substantially reduces amplitudes of noises as well as components of the acoustic sensor signal that are outside of the frequency range of the selected type heart sounds. Digitizer 124 digitizes the filtered acoustic sensor signal by sampling it at a predetermined rate. In one embodiment, the sampling rate is programmable and determined based on known frequency characteristics of the heart sounds to be detected. In one embodiment, digitizer 124 samples the acoustic sensor signal only during predetermined periods of time where the selected type heart sounds are most likely to be present. This saves electrical energy required for processing the acoustic sensor signal and/or allows a higher resolution of the digitized acoustic sensor signal without substantially increasing the electrical energy required for processing. Energy conservation is of particular importance when system 100 is a totally implantable system or includes implantable components. Digital filter 126 substantially reduces amplitudes for all components of the acoustic sensor signal except the selected type heart sounds, which are to be detected by heart sound detector 130, thereby enhancing the indications of the selected type heart sounds. In one embodiment, digital filter 126 includes a band-pass filter having cutoff frequencies determined based on the frequency spectrum of the selected type heart sounds. It is to be understood, however, that the cutoff frequencies are dependent on the purpose of detection and need not cover exactly the known spectrum of particular heart sounds. In one specific embodiment, digital filter 126 is band-pass filter having a low cutoff frequency in the range of 5 to 20 Hz and a high cutoff frequency in the range of 30 to 120 Hz selected for the purpose of detecting S3 and S4. One example of a suitable pass band for digital filter 126 for detection of S3 and S4 for monitoring ventricular diastolic hemodynamics includes a low cutoff frequency of 10 Hz and a high cutoff frequency of 60 Hz. In one specific embodiment, digital filter 126 is an envelope detector type filter. In one embodiment, digital filter 126 is a programmable digital filter in which at least one of the cutoff frequencies is programmable. This allows a dynamic selection of heart sounds for detection without a need for additional circuitry.

Cardiac sensing circuit 112 senses at least one cardiac signal indicative of cardiac electrical events that are needed for detection and measurements related to the heart sounds and/or their components. In one embodiment, the cardiac signal includes a surface ECG signal. In another embodiment, the cardiac signal includes an intracardiac ECG signal that is also referred to as an electrogram. Cardiac sensing circuit 112 includes a sensing amplifier to sense the cardiac signal, a cardiac events detector to detect the cardiac electrical events, and an event marker generator to label each detected cardiac electrical event with an event marker indicative of the timing and type of the detected cardiac electrical event. The detected electrical events include, by not limited to, selected atrial and ventricular contractions. The atrial and ventricular contractions include spontaneous contractions and artificially stimulated contractions.

Figure 2:
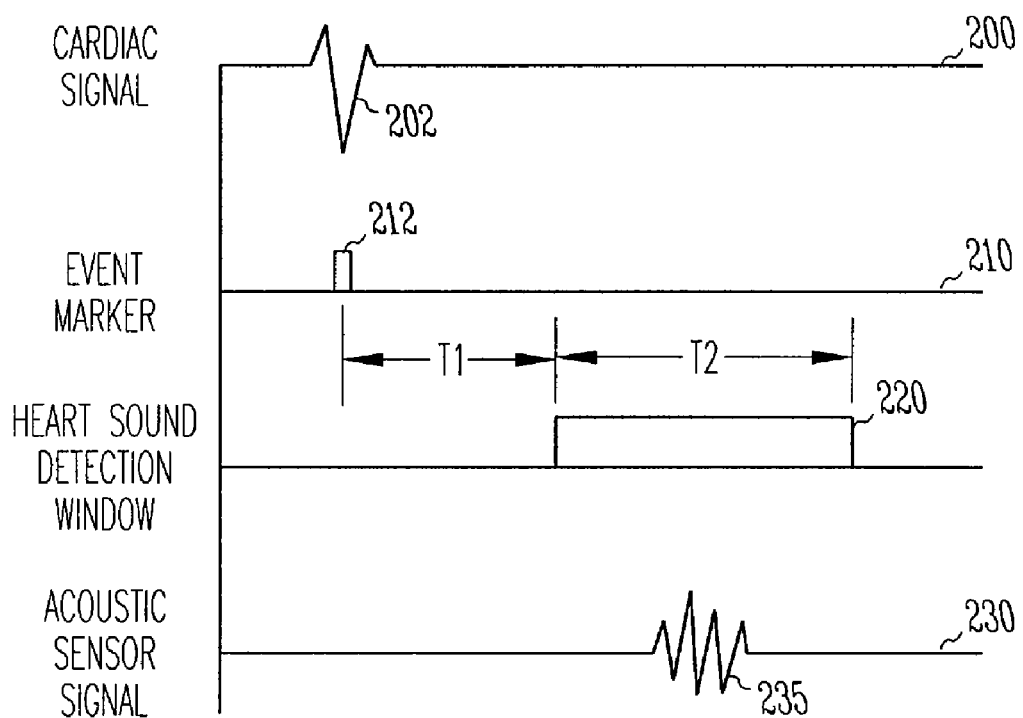
FIG. 2 is an illustration of an embodiment of a method for detecting selected heart sounds.

Heart sound detector 130 detects the selected type heart sounds. In one embodiment, heart sound detector 130 detects the selected type heart sounds based on the acoustic sensor signal. In another embodiment, heart sound detector 130 detects the selected type heart sounds based on the acoustic sensor signal and the cardiac signal sensed by cardiac sensing circuit 112. In one embodiment, heart sound detector includes a gating module 132 and a detection module 134. Gating module 132 receives the acoustic sensor signal from sensor interface module 120 and the cardiac signal from cardiac sensing circuit 112. In one embodiment, the cardiac signal received by gating module 132 includes event makers representing the detected cardiac electrical events that allow or facilitate detection of the selected type heart sounds. Gating module 132 generates heart sound detection windows each timed for detection of one of the selected type heart sounds based on a time of occurrence of one of cardiac electrical events. FIG. 2 illustrates, by way of example, but not by way of limitation, a heart sound detection window. As illustrated in FIG. 2, a cardiac signal 200 indicates a heart contraction 202. An event marker signal 210, which is a representation of cardiac signal 200, includes an event marker 212 representing heart contraction 202. An acoustic sensor signal 230, simultaneously recorded with cardiac signal 200, includes an indication of a heart sound 235. Based on available medical knowledge including statistical information available for an individual patient, heart sound 235 is substantially probable to occur within a time period T2 which starts after a time period T1 triggered by event marker 212 representing heart contraction 202. Thus, gating module 132 generates a heart sound detection window having a duration of T2 at the end of T1 following each heart contraction used for detection of the selected type heart sounds. In another embodiment, another heart sound (of a different type than the selected type) substitutes heart contraction 202 to trigger T1, and gating module 132 generates the heart sound detection window T2 at the end of T1 following each heart sound used for detection of the selected type heart sounds. In one embodiment, the heart sound detection windows are used to conserve energy and/or computational resources of system 100 by limiting the need for detection and subsequent computations to periods within the heart sound detection windows. In another embodiment, it is difficult or practically impossible to differentiate one type of the heart sounds from another by amplitude or frequency spectrum. This necessitates a method of detection that is not based on the amplitude or frequency spectrum of the selected type heart sounds. One feasible method includes the use one or more heart sound detection windows each corresponding to one or more types of heart sounds, thus allowing detections of heart sounds based on their predicted ranges of time of occurrence. Durations of the windows are determined based on an empirical study on the timing of each type of heart sounds relative to a type of cardiac. Heart sound detector 134 detects the selected type heart sounds. In one embodiment, heart sound detector 134 detects the selected type heart sounds within the one or more heart sound detection windows. In one embodiment, heart sound detector 134 includes one or more comparators to detect the selected type heart sounds by comparing the amplitude of the acoustic sensor signal during the one or more heart sound detection windows with one or more predetermined detection thresholds.

Figure 3:
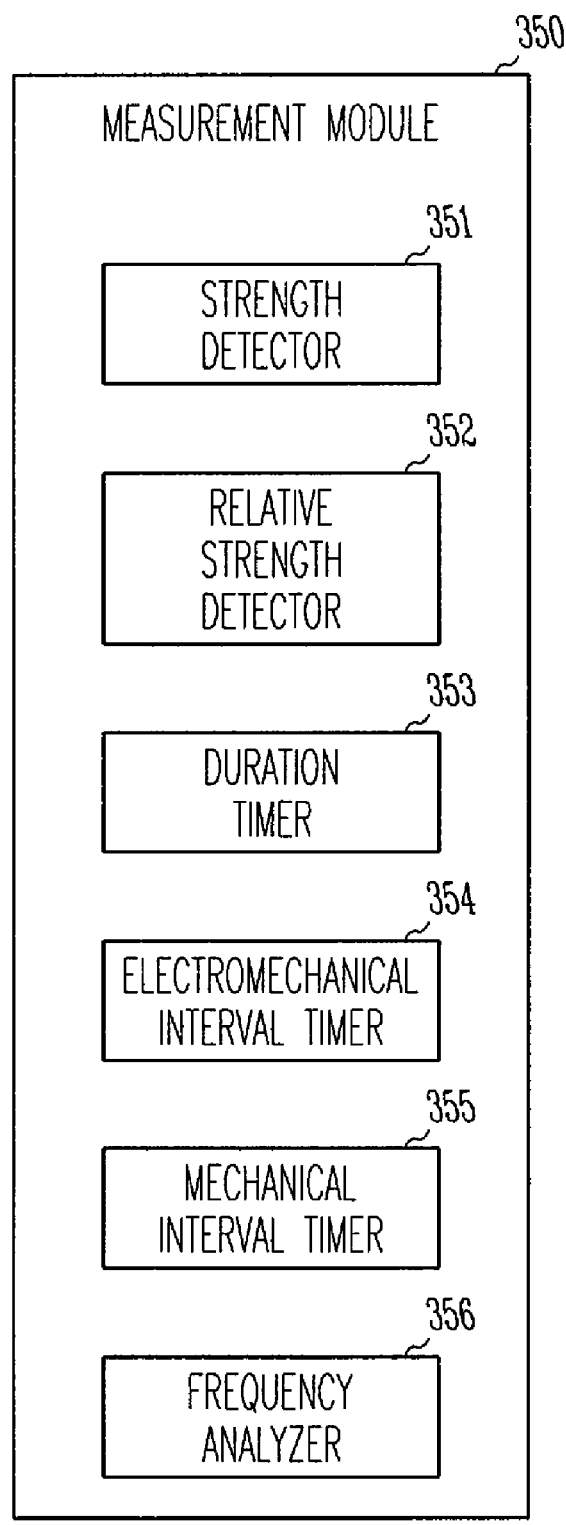
FIG. 3 is a block diagram illustrating an embodiment of a measurement module of the system of FIG. 1.

Following the detections of the selected type heart sounds by heart sound detector 130, parameter generator 140 makes measurements to generate parameter values of at least one predetermined parameter related to the detected heart sounds. In one embodiment, such a parameter value is measured from one detected heart sound. In another embodiment, the parameter value is calculated based on measurement of several detected heart sounds of the same type. The parameter values indicate the patient's hemodynamic performance, either directly or after further processing as discussed below. Parameter generator 140 includes a measurement module 150 to make measurements on the acoustic sensor signal. The measurements are timed with the detections of the selected type heart sounds. In one embodiment, measurement module 150 receives the acoustic sensor signal from heart sound detector 130 and the cardiac signal from cardiac sensing circuit 112. FIG. 3 is a block diagram that illustrates, by way of example, but not by way of limitation, components of measurement module 150. As illustrated in FIG. 3, measurement module 150 includes a strength detector 351, a relative strength detector 352, a duration timer 353, an electromechanical interval timer 354, a mechanical interval timer 355, and a frequency analyzer 356. Strength detector 351 measures amplitudes each associated with a detected heart sound. Relative strength detector 352 determines differences each between amplitudes associated with two detected heart sounds. Duration timer 353 measures durations each associated with a detected heart sound. Electromechanical interval timer 354 measures electromechanical time intervals each between a detected heart sound and a cardiac electrical event detected from the cardiac signal. Mechanical interval time 355 measures mechanical time intervals each between two detected heart sounds. Frequency analyzer 356 computes fundamental and/or harmonic frequencies each associated with a detected heart sound. In one embodiment, measurement module 150 calculate one or more parameter values each based on several values of a predetermined parameter measured by one of the components of measurement module 150. In one specific embodiment, measurement module 150 calculates the one or more parameter values each being an average of the several values of the predetermined parameter. Because of the nature and property of the acoustic sensor, the parameter values output from measurement module 150 may includes those affected by background interference. For example, when the acoustic sensor is an accelerometer, the acoustic sensor signal may indicate a patient's physical activities in addition to the heart sounds. When the acoustic sensor is a microphone, the acoustic sensor signal may indicate talking and other environment sounds in addition to the heart sounds. Thus, in one embodiment, parameter generator 140 includes a screening module 144 to exclude parameter values resulted from measurements performed when a background noise level exceeds a predetermined threshold. In one embodiment, a noise monitoring module 142 measures the background noise level. In one specific embodiment, noise monitoring module 142 includes an activity sensor that senses a patient's physical activities and an activity sensor interface module to convert the physical activities to the background noise level. In another specific embodiment, noise monitoring module includes a further sensor interface module coupled to acoustic sensor 110, which senses the patient's physical activities in addition to the acoustic energy related to the patient's cardiac mechanical activities. When acoustic sensor 110 includes an accelerometer, the further sensor interface module includes an activity level detector to produce the background noise level signal indicative of the patient's physical activities. The activity level as indicated by the acoustic sensor signal has a distinctively higher amplitude than the heart sounds. Thus, the activity level detector distinguishes the patient's physical activities from the heart sounds by using a predetermined activity level threshold. In one embodiment, parameter generator 140 includes a memory circuit 146 to store the parameter values generated by measurement module 150. In another embodiment, memory 146 stores only parameters screened by screening module 144.

Data acquisition enabler 118 controls the timing of overall data acquisition by timing the enablement of selected system components including at least one or more of acoustic sensor 110, sensor interface module 120, cardiac sensing circuit 112, heart sound detector 130, and parameter generator 140. In one embodiment, data acquisition enabler 118 enables the selected system components in response to an external command, such as given by the user. In another embodiment, data acquisition enabler 118 includes a data acquisition timer to enable the selected system components on a predetermined schedule. In one specific embodiment, the data acquisition timer enables the selected system components on a predetermined periodic basis. In another specific embodiment, if parameter generator 140 is unable to generate required parameter values on the predetermined schedule, for example, because the background noises exceeds the predetermined level when the selected system components are enabled, data acquisition enabler 118 modifies the predetermined schedule by introducing at least one delay to ensure that all the desired parameter values are obtained.

Parameter processor 160 processes the parameter values received from parameter generator 140. In one embodiment, parameter processor 160 includes a statistical processor 162, a trending analyzer 164, and an alert signal generator 166. Statistical processor 162 analyzes the parameter values generated by parameter generator 140 for a predetermined period of time. Trending analyzer 164 produces at least one trend related to the selected type heart sounds. The trend is a hemodynamic performance trend indicative of one or more cardiac conditions. In one embodiment, the trend is a plot of parameter values of one selected parameter related to the detected heart sounds over a predetermined period of time. In another embodiment, the trend is a plot of values derived for the parameter values as a result of the statistical process over the predetermined period of time. Alert signal generator 166 generates an alert signal indicative of a presence of the one or more cardiac conditions indicated by the at least one trend. In one embodiment, alert signal generator 166 includes a comparator. The comparator has a first input to receive the at least one trend, a second input representative of a predetermined threshold level, and an output indicative of the presence of the one or more clinical conditions when the at least one trend exceeds the predetermined threshold level. In one further embodiment, alert signal generator 166 includes a threshold generator that generates an adaptive threshold level based on at least one previously produced trend, such that the predetermined threshold is dynamically adjustable based on the patient's changing cardiac conditions.

Therapy circuit 170 includes, by way of example, but not by way of limitation, one or more of a pacing circuit, a defibrillation circuit, a cardiac resynchronization circuit, and a drug delivery circuit. It includes a therapy controller to execute a predetermined therapy algorithm that times therapy deliveries based on the processed cardiac signal and acoustic sensor signal. In one embodiment, the therapy controller receives at least one of selected parameter values generated by parameter generator 140, the at least one trend generated by trending analyzer 164, and the alert signal generated by alert signal generator 166, based on which it produces or adjusts one or more therapy parameters.

Figure 4:
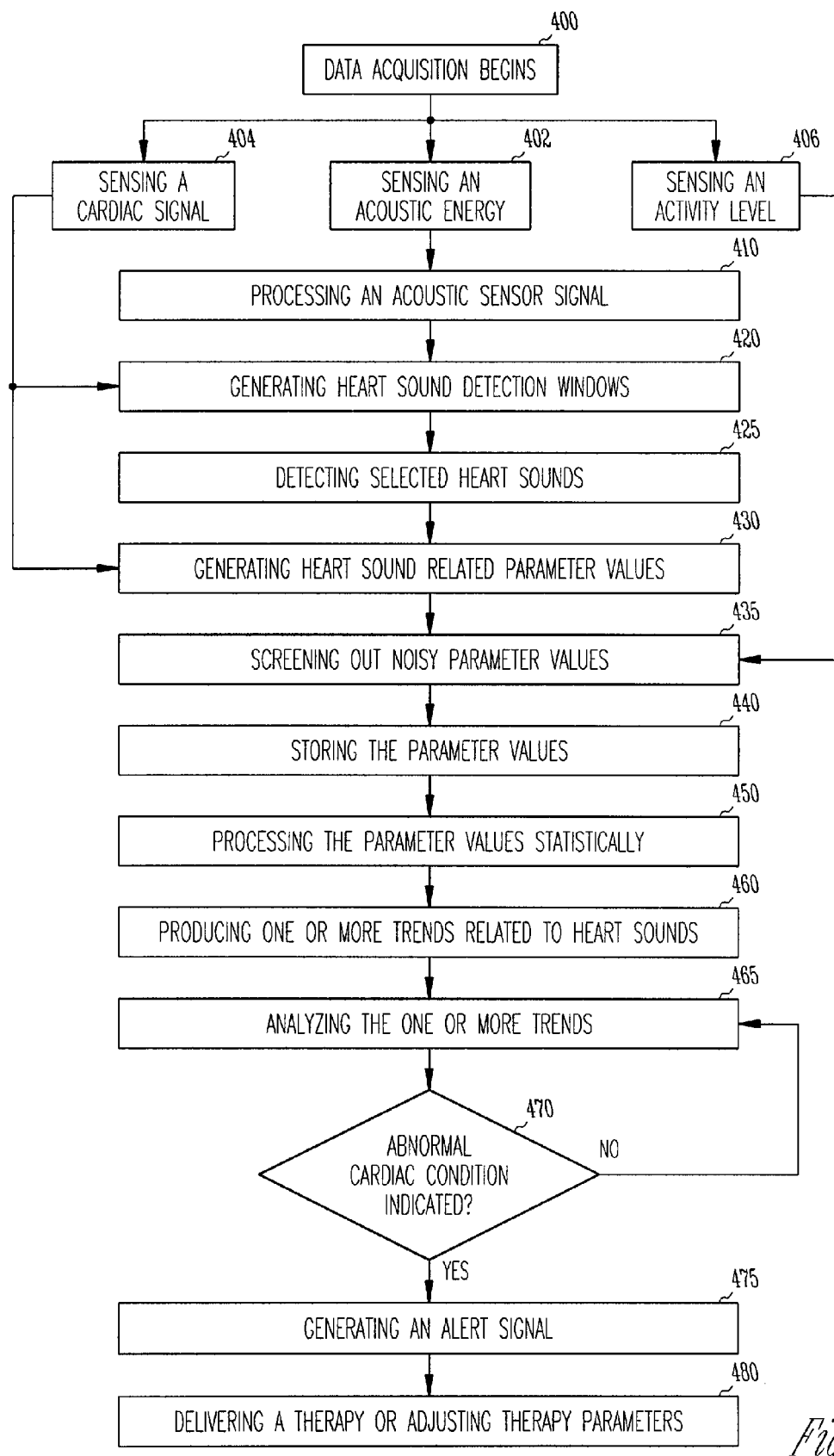
FIG. 4 is a flow chart illustrating an embodiment of a method for hemodynamics monitoring and therapy control using the system of FIG. 1.

FIG. 4 is a flow chart illustrating an embodiment of a method for hemodynamics monitoring and therapy control using system 100. At 400, data acquisition for the hemodynamics monitoring and therapy control begins. In one embodiment, the data acquisition begins as system 100 is activated. In one embodiment, the data acquisition begins in response to a user command. In another embodiment, the data acquisition begins at a predetermined time or upon a predetermined triggering event. In one embodiment, the date acquisition lasts for a predetermined duration after it begins. In one specific embodiment, the data acquisition begins on a predetermined periodic basis and lasts for a predetermined duration.

At 402, acoustic sensor 110 senses the acoustic energy related to cardiac mechanical activities and converts the acoustic energy to an acoustic sensor signal indicative heart sounds. In one embodiment, acoustic sensor 110 senses an acceleration indicative of the acoustic energy.

At 410, sensor interface module 410 processes the acoustic sensor signal to prepare for heart sound detection. In one embodiment, the acoustic sensor signal is amplified and filtered to increase its signal-to-noise ratio. Then, the acoustic sensor signal is digitized to the form of binary data. The digitized acoustic sensor signal is filtered to enhance indications of the selected type heart sounds. In one embodiment, the digitized acoustic sensor signal is filtered with at least one cutoff frequency determined based on the frequency spectrum of the selected type heart sounds.

At 420, heart sound detector 130 generates heart sound detection windows each timed for detecting one of the selected type heart sounds. The heart sound detection windows are each triggered by one of selected cardiac electrical events detected from the cardiac signal sensed at 404. In one embodiment, the selected cardiac electrical events include at least one of spontaneous or artificially stimulated atrial and ventricular contractions. In one embodiment, the selected cardiac electrical events are each represented by a predetermined event marker. In one specific embodiment, At 425, the selected type heart sounds are detected. In one embodiment, each of the selected type heart sounds is detected when the amplitude of the acoustic sensor signal exceeds a predetermined threshold level.

At 430, parameter generator 140 generates the parameter values of at least one parameter related to the detected heart sounds based on the acoustic sensor signal produced at 400 and/or the cardiac signal sensed at 404. Such parameter values include, by way of example, but not by way of limitation, one or more of (i) an amplitude associated with one or one selected type of the selected type heart sounds; (ii) a relative strength being differences between amplitudes associated with two or two selected types of the selected type heart sounds; (iii) a duration associated with one or one selected type of the selected type heart sounds; (iv) an electromechanical time intervals between one or one selected type of the selected type heart sounds and one or one type of selected type cardiac electrical events; (v) a mechanical time interval between two or two selected types of the selected type heart sounds; and (vi) a fundamental or harmonic frequency associated with one or one selected type of the selected type heart sounds. In one embodiment, parameter values related to S3 and/or S4 are measured and/or calculated for the purpose of monitoring ventricular diastolic hemodynamic performance. The parameter values of one or more of the following parameters are generated: (i) peak amplitude of S3; (ii) time of onset of S3 relative to onset of S2; (iii) duration of S3; (iv) fundamental frequency if S3; (v) time of occurrence of S3 relative to the subsequently adjacent atrial contraction; (vi) peak amplitude of S4; (vii) time interval between atrial contraction and the subsequently adjacent S4; (viii) fundamental frequency of S4; (ix) duration of S4; (x) time of occurrence of S4 relative to the subsequently adjacent ventricular contraction; and (xi) amplitude of S4 relative to amplitude of S3. In one embodiment, parameter generator 140 screens out noisy values of the parameter values measured at 435. Such noisy values include parameter values measured when the background noise level exceeds a predetermined threshold. In one embodiment, the patient's physical activities are sensed at 406 to produce an activity level signal indicative of the background noise level. In one specific embodiment, the activity level signal is derived from the same acoustic sensor signal from which the selected type heart sounds are detected. This is possible because the patient's physical activities are typically indicated with amplitudes that are distinctively higher than the amplitudes of the selected type heart sounds.

At 440, the parameter values are stored in memory circuit 146 or other storage medium. In one embodiment, system 1 00 uses the parameter values directly to control delivery of at least one therapy with at least one therapy parameter being a function of the parameter values. In another embodiment, the parameter values are further processed and analyzed by system 100 for monitoring, diagnosis, and/or therapy control purposes. In yet another embodiment, the stored parameter values are transferred to another system, such as a computer separated from system 100, for further processing and/or analysis.

At 450, parameter processor 160 statistically processes the parameter values. The statistical process includes analyzing the parameter values of the at least one parameter related to the detected heart sounds in relation to historical values of that parameter measured during a predetermined period of time. The outcome of the statistical process reveals changes in cardiac conditions reflected in the characteristics of the selected type heart sounds. In one embodiment, the outcome of the statistical process reveals changes in ventricular diastolic filing patterns during the predetermined period of time. In one specific embodiment, the predetermined period of time ranges from 1 day to 3 months.

At 460, parameter processor 160 produces at least one hemodynamic performance trend related to the selected type heart sounds. In one embodiment, parameter processor 160 produces the at least one trend based on the outcome of the statistical analysis. In one embodiment, one or more trends quantitatively present one or more ventricular diastolic filing pattern changes during a predetermined duration. In one embodiment, parameter processor 160 plots the parameter values of the at least one parameter related to the detected heart sounds versus time. In another embodiment, parameter processor 160 statistically processes the parameter values of the at least one parameter related to the detected heart sounds and plots the result. At 465, the one or more trends are analyzed for indication of cardiac conditions. In one embodiment, the values of each trend are compared to a predetermined threshold level, and a predefined cardiac condition is indicated when any value exceeds the predetermined threshold level. In one embodiment, the predetermined threshold level is determined based on at least one previously produced trend.

At 475, an alert signal is generated when a cardiac condition is indicated by the at least one hemodynamic performance trend at 470. The alert signal notifies the user of the cardiac condition that may need medical attention. In one embodiment, the cardiac condition requires delivery of a therapy. In another embodiment, the alert signal indicates a need for changing one or more therapy parameters.

In one embodiment, a therapy is delivered in response to the alert signal at 480. The therapy includes one or more of, for example, a pacing therapy, a defibrillation therapy, a cardiac resynchronization therapy, any other electrical stimulation therapy, and a drug therapy. The type of the therapy as therapy parameters are determined based on the at least one trend and/or selected values of the at least one parameter related to the detected heart sounds. In one specific embodiment, therapy circuit 170 delivers the therapy. In another embodiment, one or more therapy parameters are adjusted in response to the alert signal, and the new therapy parameters are determined based on the at least one trend and/or the selected values of the at least one parameter related to the detected heart sounds. In an alternative embodiment, the therapy delivery or the therapy parameter adjustments are not dependent on the alert signal. The at least one trend and/or the selected values of the at least one parameter related to the detected heart sounds directly determine the need for the therapy delivery or the therapy parameter adjustments.

Many embodiments combining the present method with available medical knowledge will be apparent to those of skill in the art. In one example, the fundamental frequency (also referred to as the pitch) of S3 is correlated to the stiffness of the left ventricular wall during the rapid filling phase of diastole. The wall stiffness is proportional to diastolic pressure in the left ventricle and to the thickness of the left ventricular wall. Therefore, an increase in the pitch of S3 is used to indicate one or more of an elevated left ventricular filling pressure and a thickened left ventricular wall. The elevation of the left ventricular filling pressure and/or the increase of the left ventricular wall thickness may reach a degree, represented by predetermined thresholds of S3 fundamental frequency, that requires an application of adjustment of a therapy. In another example, the amplitude of S3 is directly related to the rate of deceleration of blood flow into the left ventricle during the rapid filling phase of diastole. An increase in amplitude of S3 can be used to indicate an elevation of left atrial filling pressure, an increase in stiffness of the left ventricle, or both, which represent a restrictive filling pattern associated with heart failure. Therefore, the trend of S3 amplitude is useful in monitoring cardiac mechanical properties related to heart failure. In yet another example, the elevated filling pressures cause pulmonary edema. Thus, a physician determines the need of a drug therapy to relieve the elevated pressures based on one or more trends of parameters related to S3. These are a few examples, among many possible embodiments, illustrating how system 100 is used. In general, trends of any of the measured parameter values can be used individually, jointly, and/or in combination with other trends related to cardiac functions.

Figure 5:
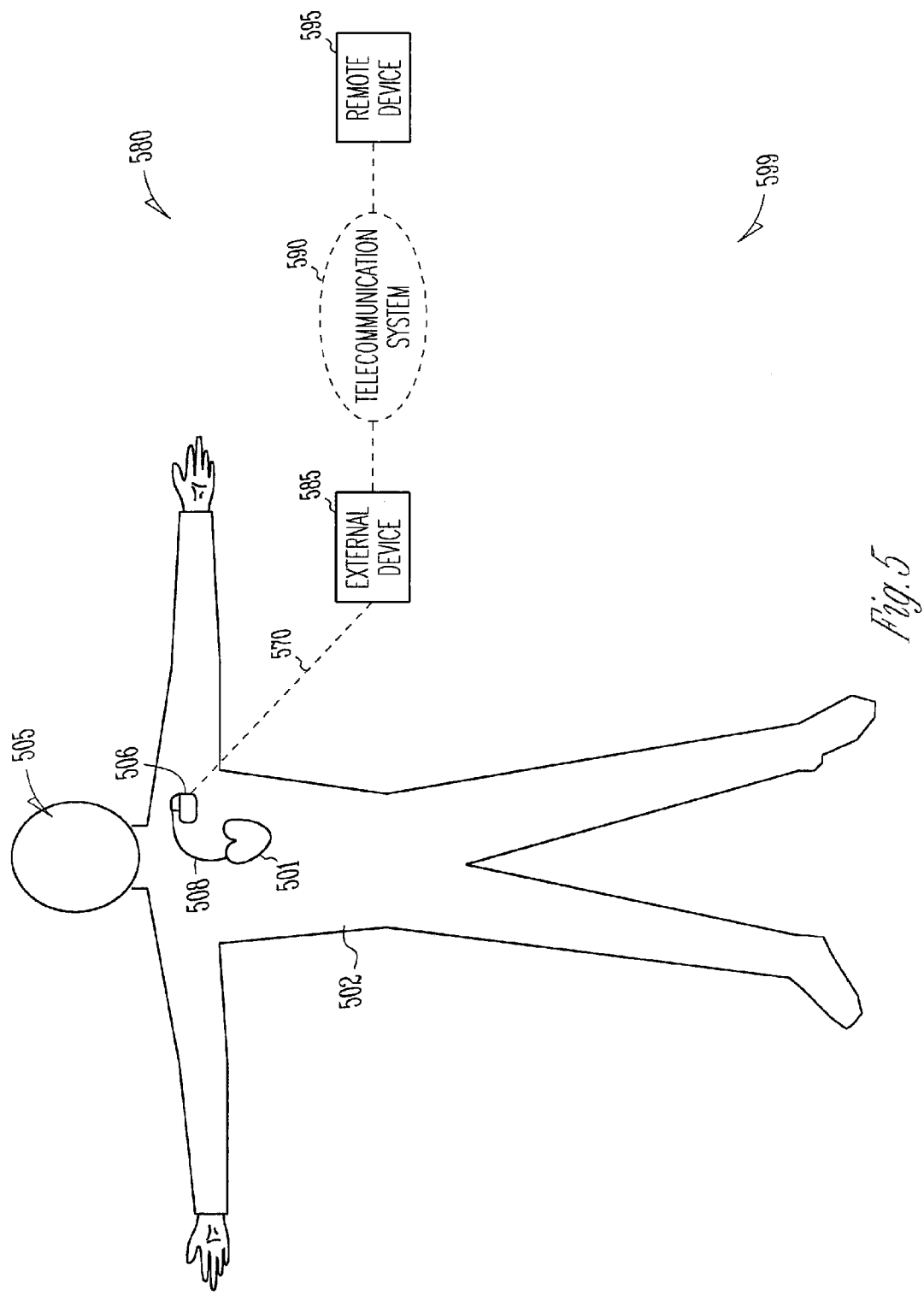
FIG. 5 is an illustration of an embodiment of portions of a cardiac rhythm management system incorporating heart-sound based hemodynamics monitoring and therapy control and portions of an environment in which it is used.

FIG. 5 is an illustration of an embodiment of portions of a cardiac rhythm management system 599 and portions of an environment in which it is used. System 599 incorporates a heart-sound based hemodynamics monitoring and therapy control system such as system 100. In one embodiment, cardiac rhythm management system 599 includes an implanted system 505, an external system 580, and a telemetry link 570 providing for communication between implanted system 505 and external system 580. Implanted system 505 includes an implanted device 506 and a lead system 508. Implanted device 506 is implanted within a patient's body 502 and coupled to the patient's heart 501 via lead system 508. Examples of implanted device 506 include pacemakers, cardioverter/defibrillators, pacemaker/defibrillators, cardiac resynchronization devices, and drug delivery devices. External system 580 is a patient management system including an external device 585 in proximity of implanted device 502, a remote device 595 in a relatively distant location, and a telecommunication system 590 linking external device 585 and remote device 595. An example of such a patient management system is discussed in Hatlestad et al., "ADVANCED PATIENT MANAGEMENT FOR DEFINING, IDENTIFYING AND USING PREDETERMINED HEALTH-RELATED EVENTS," application Ser. No. 10/323,604, filed on Dec. 18, 2002, assigned to Cardiac Pacemakers, Inc., the specification of which is incorporated herein by reference in its entirety. In one embodiment, telemetry link 570 is an inductive telemetry link. In an alternative embodiment, telemetry link 570 is a far-field radio-frequency telemetry link. In one embodiment, telemetry link 570 provides for data transmission from implanted device 506 to external device 585. This may include, for example, transmitting real-time physiological data acquired by implanted device 506, extracting physiological data acquired by and stored in implanted device 506, extracting therapy history data stored in implanted device 506, and extracting data indicating an operational status of implanted device 506 (e.g., battery status and lead impedance). In a further embodiment, telemetry link 570 provides for data transmission from external device 585 to implanted device 506. This may include, for example, programming implanted device 506 to acquire physiological data, programming implanted device 506 to perform at least one self-diagnostic test (such as for a device operational status), and programming implanted device 506 to deliver at least one therapy.

In one embodiment, programming implanted device 506 includes sending therapy parameters to implantable device 506. The therapy parameters provide an improved hemodynamic performance for a patient by delivering cardiac pacing pulses to the patient's heart. In one embodiment, the therapy parameters providing for the improved hemodynamic performance are determined by monitoring one or more ventricular diastolic hemodynamics as indicated by parameters related to heart sounds such as S3 and S4. Such parameters indicate the heart's mechanical activities and electromechanical association. In one specific embodiment, the acquisition of values of such parameters, the processing of the parameter values, and the subsequent determination of the therapy parameters are performed by system 100, as discussed above with reference to FIGS. 1-3.

Figure 6:
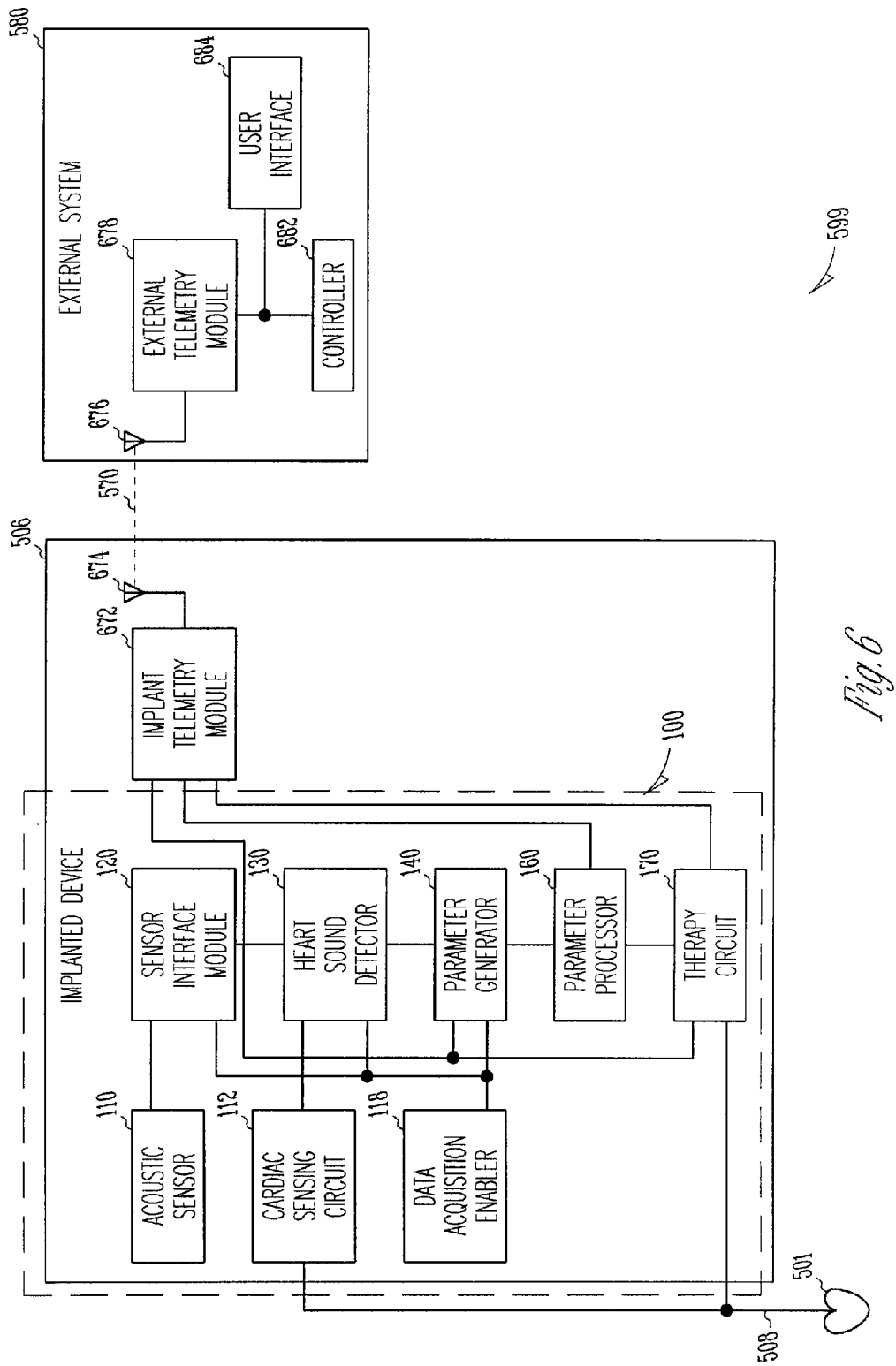
FIG. 6 is a block diagram illustrating a specific embodiment of portions of the cardiac rhythm management system of FIG. 5.

FIG. 6 is a block diagram illustrating a specific embodiment of portions of cardiac rhythm management system 599. In this embodiment, system 100 is substantially included within implanted device 506. System 100 includes, as discussed above with reference to FIG. 1, acoustic sensor 110, sensor interface module 120, cardiac sensing circuit 112, heart sound detector 130, parameter generator 140, data acquisition timer 118, parameter processor 160, and therapy circuit 170. Implanted device 506 also includes, among other things, an implant telemetry module 672 and an implant antenna 674 to provide implanted device 506 with telemetry capability allowing it to communicate with external system 580 via telemetry link 570. In one embodiment, therapy circuit 170 includes a therapy controller that executes a predetermined therapy control algorithm to determine whether to deliver a therapy or adjust one or more therapy parameters based on the one or more of the heart sound-related parameter values generated by parameter generator 140 and trends and alert signal generated by parameter processor 160.

External system 580 includes, among other things, an external antenna 676, an external telemetry module 678, a controller 682, and a user interface 684. In one embodiment, external telemetry module 678 and external antenna 676 are included in external device 585 to provide external system 580 with capability of communicating with implanted device 506 through telemetry link 570 and external device 585. Controller 682 controls telemetry operation of external system 580, processes signals received from implanted device 506 for presentation on user interface 684, and processes user commands entered through user interface 684 for transmission to implanted device 506. In one embodiment, one or more of the heart-sound related parameter values, trends, and alert signal, as discussed above, are acquired by system 100 and telemetered to external system 580 via telemetry link 570. Controller 682 executes a predetermined therapy control algorithm to determine whether to deliver a therapy or adjust one or more therapy parameters based on the one or more of the heart sound-related parameter values, trends, and alert signal.

In one embodiment, system 100 is completely within a hermetically sealed can that houses at least portions of implanted device 506. Housing acoustic sensor 110 in the can has the advantage of minimizing the background noise associated with physical movements of the sensor, especially when acoustic sensor 110 includes an accelerometer. In another embodiment, acoustic sensor 110 is attached to a lead of lead system 508. This allows disposition of acoustic sensor 110 in or near heart 501 such that it is near the mechanical activities being the sources of the heart sounds of interest.

To include substantially the whole system 100 within implanted device 506 provides for the advantage of a self-contained implantable cardiac rhythm management system incorporating heart-sound based therapy control. In one embodiment, the heart-sound based therapy control using system 100 is able to function without telemetry link 570, for example, when the patient is outside the range of the telemetry communication. Implanted device 506 determines, without the intervention of the user or controller 682, whether to deliver a therapy or adjust one or more therapy parameters based on the one or more of the parameter values, trends, and alert signal generated within itself by system 100.

Figure 7:
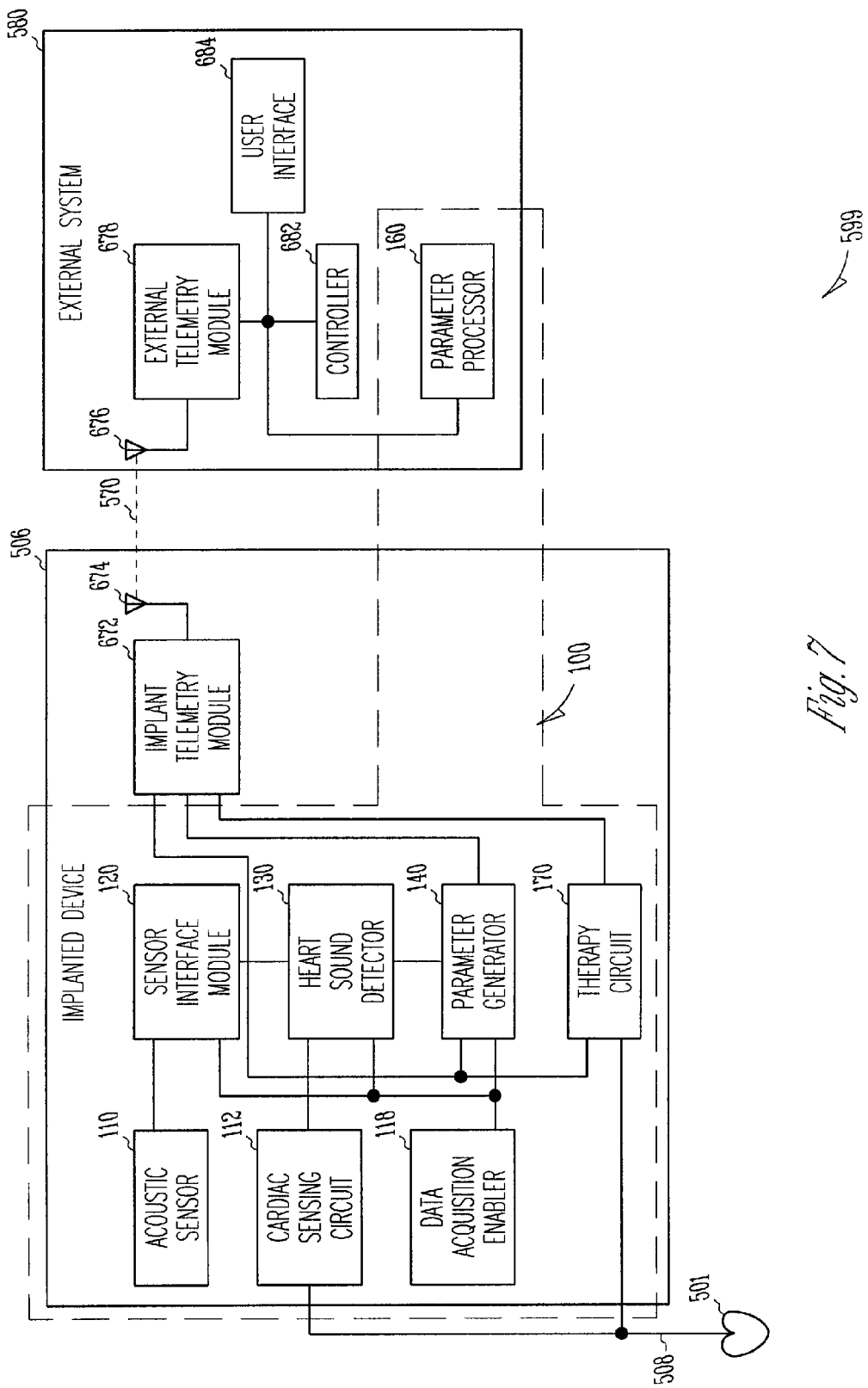
FIG. 7 is a block diagram illustrating another specific embodiment of portions of the cardiac rhythm management system of FIG. 5.

FIG. 7 is a block diagram illustrating another specific embodiment of portions of cardiac rhythm management system 599. In this embodiment, system 100 is partially included within implantable device 506 and partially included in external system 580. In one specific embodiment, parameter processor 160 is within external system 580, and the remaining components of system 100 are within implanted device 506. Parameter values generated by parameter generator 140 are telemetered to external system 580 via telemetry link 570 for further processing by parameter processor 160. In one embodiment, parameter processor 160 is included in external device 585. In an alternative embodiment, parameter processor 160 is included in remote device 595.

In one embodiment, the parameter values are telemetered as they are generated. In another embodiment, parameter values are first stored in memory circuit 146. Data acquisition enabler 118 times transmission of the parameter values in response to a command from external device 580 or on a predetermined schedule.

To include parameter processor 160 in external system 580 avoids placing the demand of energy and circuit resources required by parameter processor 160 in implanted device 506, which is subject to design restraints including power and size limitations. The advantages also include the feasibility of updating parameter processing algorithms used by parameter processor 160 without the need of replacing implanted device 506.

It is to be understood that the above detailed description is intended to be illustrative, and not restrictive. For example, system 100 may be incorporated into any implanted or external medical device providing for ECG and heart sound monitoring. Other embodiments will be apparent to those of skill in the art upon reading and understanding the above description. The scope of the invention should, therefore, be determined with reference to the appended claims, along with the full scope of equivalents to which such claims are entitled.

OTHER EXAMPLES

Generally, heart sounds, e.g., S3, are correlated to heart function. Typically, heart failure arises when the pumping of the heart is compromised. As heart failure worsens, for various reasons, the pumping function of the heart typically deteriorates. As the pumping function of the heart deteriorates, the demand for blood to the body generally increases, typically resulting in an increased left atrial pressure. As the demand for blood to the body increases and the pumping function of the heart deteriorates, fluid typically builds in the lungs. Generally, as fluid builds in the lungs, the demand for increased blood through the heart increases, also typically resulting in an increased left atrial pressure. Thus, increased atrial pressure, including left atrial pressure, is an indicator of heart failure.

A system and method have been developed to correlate one or more than one heart sound, e.g., S3, to atrial filling pressure, including left atrial filling pressure, and provide an alert, such as when high atrial filling pressure is detected. An increase of S3 amplitude, or another measurement, feature, characteristic, computation, or interval of a heart sound signal, can be used to indicate an elevation of left atrial filling pressure. Therefore, the trend of S3 amplitude, or value of another measurement, feature, characteristic, computation, or interval of the heart sound signal, is useful in monitoring cardiac mechanical properties related to heart failure.

Using one or a combination of a measurement, feature, characteristic, computation, or interval of the heart sound signal, a high filling pressure can be detected, including a high atrial filling pressure, or a high left atrial filling pressure. Using the detected pressure, an alert can be provided, such as for example when the pressure is detected above an absolute pressure threshold, e.g., 25 mmHg. Other alerts can also be provided, such as discussed elsewhere in this document.

Figure 8:
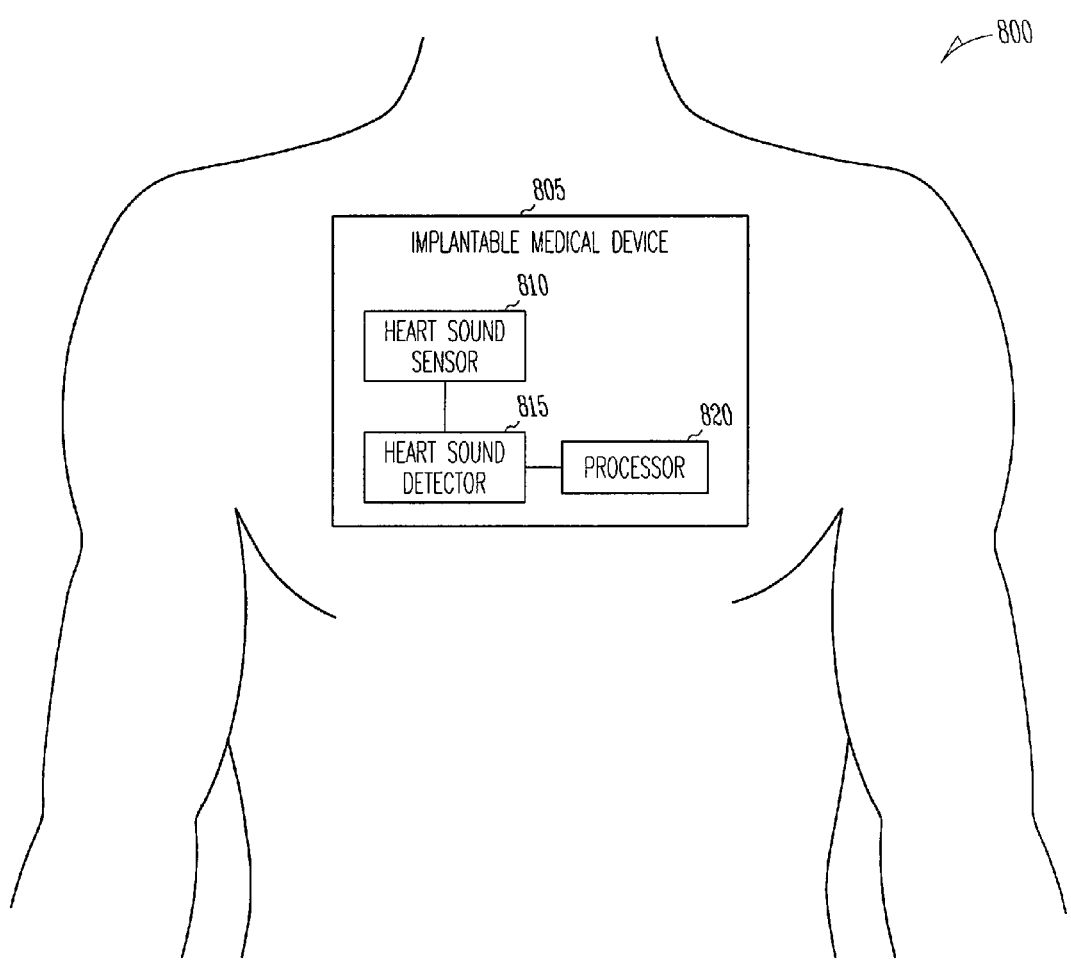
FIG. 8 illustrates generally an embodiment of a system including an implantable medical device, which includes a heart sound sensor, a heart sound detector, and a processor.

FIG. 8 illustrates generally an example of portions of a system 800 that includes an implantable medical device 805, which includes a heart sound sensor 810, a heart sound detector 815, and a processor 820. In other examples, the heart sound detector 815, or the processor 820, can be an implantable component external to the implantable medical device 805, or can be an external component.

In this example, the heart sound sensor 810 is configured to sense a heart sound signal of a heart. The heart sound signal of the heart can include any signal indicative of a heart sound of the heart. Illustrative examples of heart sounds include one or more than one of an S1 heart sound, an S2 heart sound, an S3 heart sound, an S4 heart sound, a regurgitant heart murmur, a stenotic heart murmur sound, and a coronary vascular blood turbulence sound. The heart sound sensor 810 can be any device configured to sense the heart sound signal of the heart, e.g., an accelerometer, a microphone, etc. The heart sound sensor 810 can transduce the heart sound, such as into an electrical or optical "heart sound" signal that includes information about the sensed heart sound.

In the example of FIG. 8, the heart sound detector 815 is coupled to the heart sound sensor 810. In this example, the heart sound detector 815 is generally configured to detect at least one parameter indicative of an atrial filling pressure of the heart using the heart sound signal. In an example, the at least one parameter indicative of an atrial filling pressure includes at least one heart sound parameter indicative of an atrial filling pressure.

In this example, the processor 820 is coupled to the heart sound detector 815. The processor 820 is generally configured to compare the at least one parameter indicative of an atrial filling pressure to a threshold. In certain examples, the threshold can include a population-based threshold, a specified threshold, an adjustable threshold, an absolute threshold, or a permutation or combination of one or more than one threshold. In certain examples, where the threshold is an adjustable threshold, the adjustable threshold can include an automatically adjustable threshold, such as by the processor 820 in response to other information, e.g., the posture signal, etc., a user adjusted threshold, or a manufacturer adjusted threshold. In an example, the processor 820 compares the at least one parameter to the threshold to determine if the at least one parameter has crossed or is across the threshold. In certain examples, the at least one parameter has crossed the threshold if the at least one parameter is of a level that is equal to or below the threshold, or if the at least one parameter is of a level that is equal to or above the threshold. In other examples, the at least one parameter is across the threshold if the at least one parameter is of a level that is equal to or below the threshold, or if the at least one parameter is of a level that is equal to or above the threshold.

In certain examples, the system 800 can operate in an ongoing fashion (e.g., continuously), the system 800 can operate one or more than one time during one or more than one time period, e.g., one or more than one time per hour, one or more than one time per day, etc., or the system 800 can operate or cease to operate using a triggering event, including a user or patient input, or a physiological or other sensor input.

Figure 9:
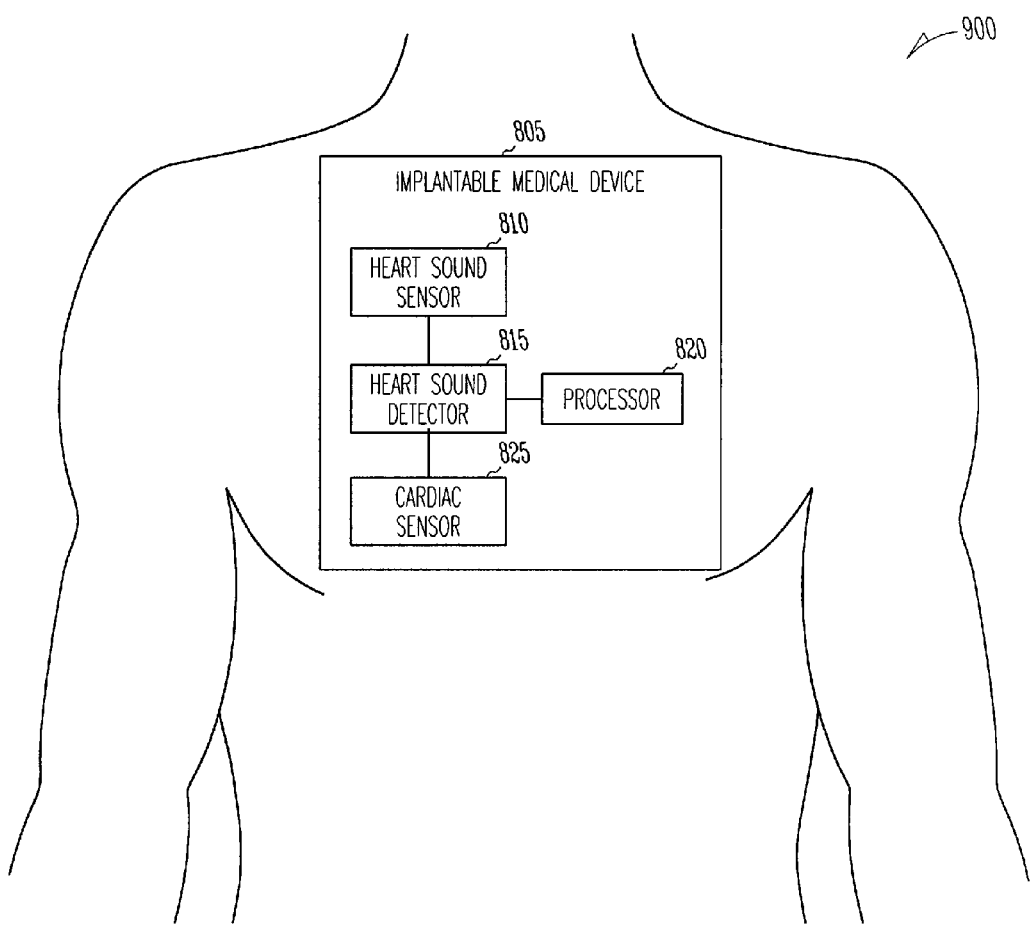
FIG. 9 illustrates generally an embodiment of a system including an implantable medical device, which includes a heart sound sensor, a heart sound detector, a cardiac sensor, and a processor.

FIG. 9 illustrates generally an example of a system 900 that includes an implantable medical device 805, which includes a heart sound sensor 810, a heart sound detector 815, a processor 820, and a cardiac sensor 825. In other examples, the heart sound detector 815, or the processor 820, can be an implantable component external to the implantable medical device 805, or can be an external component.

In this example, the cardiac sensor 825 is coupled to the heart sound detector 815. The cardiac sensor is generally configured to sense a cardiac signal of the heart. The cardiac signal of the heart can include any signal indicative of the electrical or mechanical cardiac activity of the heart, e.g., an electrocardiogram (ECG) signal, an impedance signal, an acceleration signal, etc. The cardiac sensor 825 can include any device configured to sense the cardiac activity of the heart, e.g., an intrinsic cardiac signal sensor, such as one or more than one electrode or lead to sense one or more than one depolarization, a mechanical sensor, such as an impedance sensor or an accelerometer to sense one or more than one contraction.

In the example of FIG. 9, the heart sound detector 815 is configured to detect at least one parameter indicative of an atrial filling pressure of the heart using the heart sound signal and the cardiac signal. In an example, the heart sound detector 815 receives the heart sound signal from the heart sound sensor 810 and receives the cardiac signal from the cardiac sensor 825. In an example, the heart sound detector 815 uses information from the cardiac signal, such as to time or gate or otherwise assist detection of at least one heart sound, e.g., S1, S2, etc.

Figure 10:
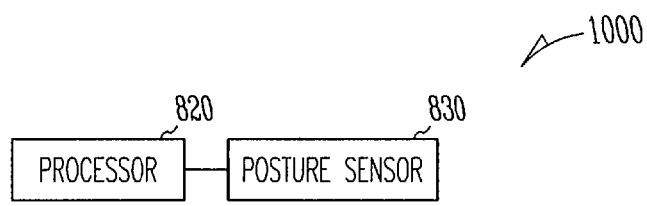
FIG. 10 illustrates generally an embodiment of a system including a processor and a posture sensor.

FIG. 10 illustrates generally an example of a system 1000 including a processor 820 and a posture sensor 830. In an example, the system 1000 includes an implantable medical device 805, which includes the processor 820 and the posture sensor 830. In other examples, the processor 820, or the posture sensor 830, can be an implantable component external to the implantable medical device, or can be an external component.

In the example of FIG. 10, the posture sensor 830 is coupled to the processor 820. The posture sensor 830 is generally configured to sense a posture signal indicative of a posture or an activity level of a patient. In an example, the processor 820 is configured to determine, set, or adjust a threshold using information from the posture sensor 830. In another example, the processor 820 is configured to determine or adjust at least one parameter indicative of an atrial filling pressure of a heart using information from the posture sensor 830. In certain examples, the posture sensor 830 includes at least one of an accelerometer, a pendulum-type device, a tilt switch, and a pressure sensor, or the posture sensor 830 includes a permutation or combination of one or more than one of the accelerometer, the pendulum-type device, and the pressure sensor. In an example, the processor 820 can determine the activity of the patient using the posture sensor 830, e.g., using information from the most current posture signal and at least one previous posture signal.

Figure 11:
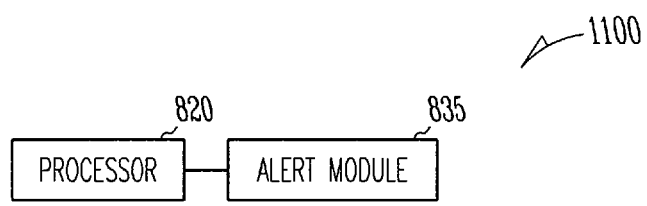
FIG. 11 illustrates generally an embodiment of a system including a processor and an alert module.

FIG. 11 illustrates generally an example of a system 1100 that includes a processor 820 and an alert module 835. In an example, the system 1100 includes an implantable medical device 805, which includes the processor 820 or the alert module 835. In other examples, the processor 820, or the alert module 835, can be an implantable component external to the implantable medical device, or can be an external component.

In the example of FIG. 11, the alert module 835 is coupled to the processor 820. The alert module 835 is generally configured to alert a user or a patient using at least one parameter indicative of an atrial filling pressure of a heart. In certain examples, the alert module 835 is configured to alert the patient, such as by generating a noise or a vibration. In other examples, the alert module 835 is configured to alert the user or patient, such as by communicating a notification to the user or patient, e.g., communicating a notification to the user or patient directly, or communicating a notification to the user or patient through some external device, such as an external programmer. In an example, the alert module 835 is configured to communicate with a remote user interface, such as the LATITUDE configuration. In another example, the alert module 835 is configured to communicate to an external device, e.g., an external repeater, which can be configured to communicate to an external repeater. In another example, the external repeater can be configured to communicate, such as by an e-mail or other communication, to the user.

Figure 12:
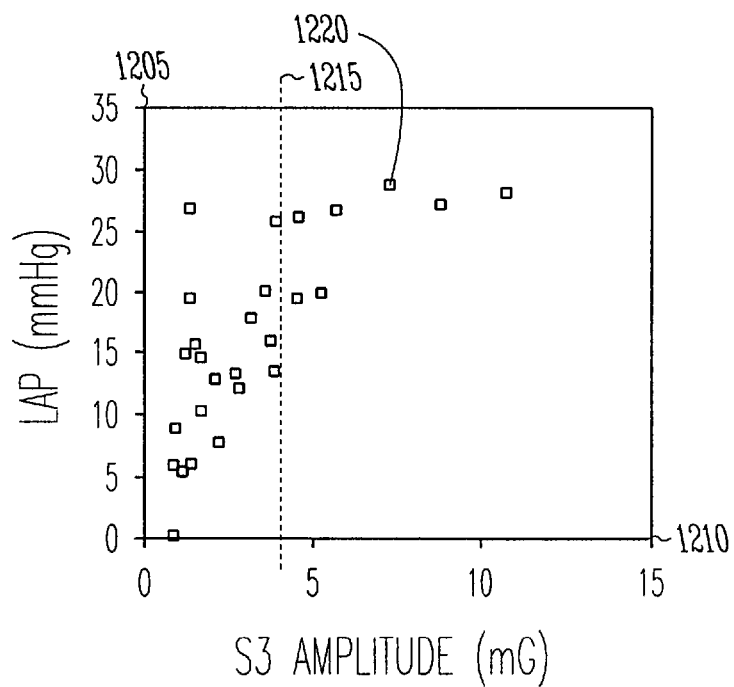
FIG. 12 illustrates generally an embodiment of a relationship between left atrial pressure (LAP) and the amplitude of the third heart sound (S3).

FIG. 12 illustrates generally an example of a relationship between left atrial pressure (LAP) 1205 and the amplitude of the third heart sound (S3) 1210. In an example, a data point 1220 includes an S3 amplitude value and an LAP value. As is shown in FIG. 12, generally, as the LAP 1205 increases, the S3 amplitude 1210 increases.

In an example, using the data of FIG. 12, an S3 threshold 1215 can be set at 4 mG. In this example, an LAP of 25 mmHg or higher can be detected with a sensitivity of 71% (5/7) and a specificity of 90% (2/20), or an LAP of 20 mmHG or higher can be detected with a sensitivity of 64% (7/11) and a specificity of 100% (0/16). In another example, using the data of FIG. 12, the S3 threshold 1215 can be set at 2 mG. In this example, an LAP of 10 mmHg or higher can be detected with a sensitivity of 75% (15/20) and a specificity of 86% (1/7).

Figure 13:
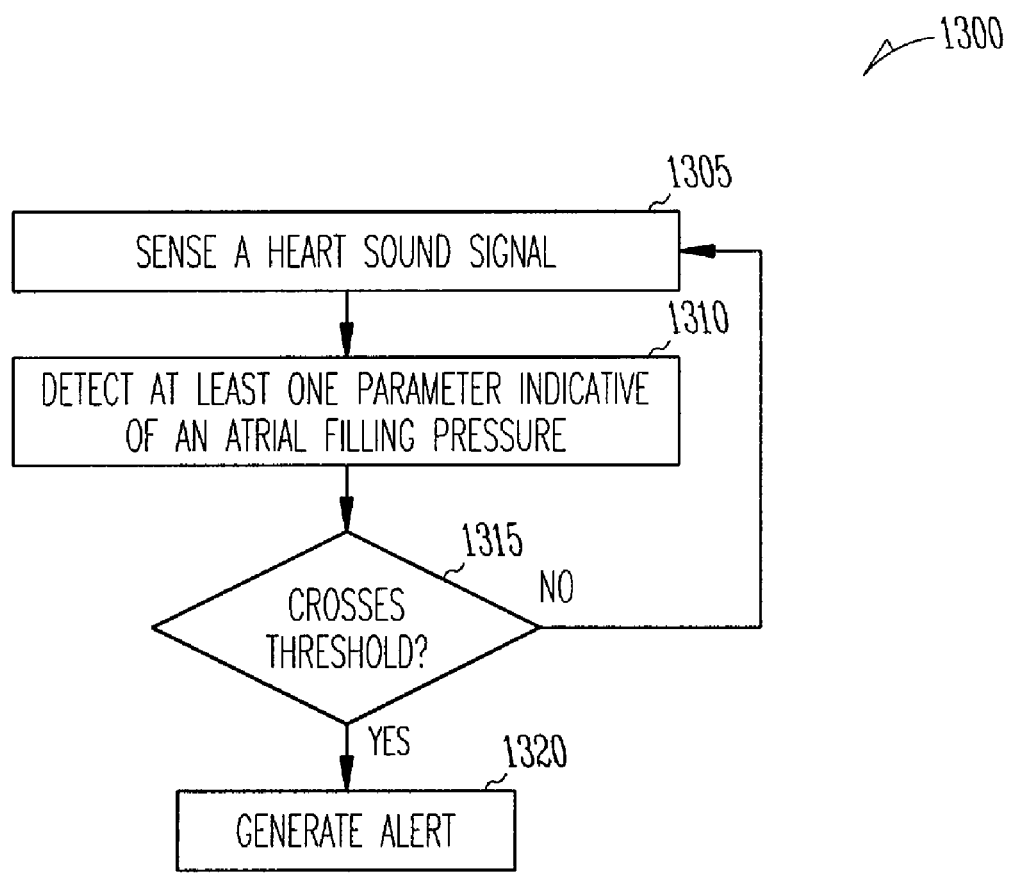
FIG. 13 illustrates generally an embodiment of a method including sensing a heart sound signal, detecting at least one parameter indicative of an atrial filling pressure, and generating an alert when the at least one parameter indicative of an atrial filling pressure crosses a threshold.

FIG. 13 illustrates generally an example of a method 1300 including sensing a heart sound signal, detecting at least one parameter indicative of an atrial filling pressure, and generating an alert when the at least one parameter indicative of an atrial filling pressure crosses a threshold. In an example, the method 1300 can operate in an ongoing or continuous manner, the method 1300 can operate one or more than one particular time during one or more than one time period, e.g., one or more than one time per hour, one or more than one time per day, etc., or the method 1300 can operate or cease to operate using a triggering event, including a user or patient input.

At 1305, a heart sound signal is sensed. The heart sound signal can include any signal indicative of a heart sound of a heart. In an example, the heart sound signal can be sensed using the heart sound sensor 810.

At 1310, at least one parameter indicative of an atrial filling pressure is detected. In an example, the at least one parameter indicative of an atrial filling pressure is detected using the heart sound signal.

Generally, the at least one parameter indicative of an atrial filling pressure can include at least one measurement, feature, characteristic, computation, or interval of the heart sound signal. In certain examples, the at least one measurement, feature, characteristic, computation, or interval of the heart sound signal includes at least one of an amplitude of a heart sound, a magnitude of a heart sound, a total energy of a heart sound, an interval between one heart sound feature and another heart sound feature, at least one heart sound characteristic normalized by at least one other heart sound characteristic, etc. (e.g., an amplitude or magnitude of S1, an amplitude or magnitude of S2, an amplitude or magnitude of S3, an amplitude or magnitude of S4, the existence of a split-S2, a split-S2 time interval, a S1-S2 time interval, a S2-S3 time interval, a characteristic of S3 normalized by a characteristic of S1, etc.).

At 1315, the method 1300 determines if the at least one parameter indicative of an atrial filling pressure has crossed, or is across, the threshold. In an example, at 1315, the processor 820 determines if the at least one parameter indicative of an atrial filling pressure has crossed the threshold. In an example, if, at 1315, the at least one parameter indicative of an atrial filling pressure crosses the threshold, then an alert is generated at 1320. In another example, if, at 1315, the at least one parameter indicative of an atrial filling pressure is of a level equal to or above the threshold, then an alert is generated at 1320. In another example, if, at 1315, the at least one parameter indicative of an atrial filling pressure is of a level equal to or below the threshold, then an alert is generated at 1320. In certain examples, the at least one parameter indicative of an atrial filling pressure can be across the threshold for a certain duration (e.g., one or more than one cardiac cycle, one or more than one minute, one or more than one hour, one or more than one day, etc.) before the alert module is configured to generate an alert, or the at least one parameter indicative of an atrial filling pressure can cross the threshold for a certain duration (e.g., the at least one parameter crosses the threshold one time per day for 3 consecutive days, the at least one parameter crosses the threshold one time per day for 5 consecutive days, etc.) before the alert module is configured to generate an alert.

Generally, generating an alert using a population-based or absolute threshold allows the user or the processor 820 to set or adjust the threshold to detect a condition with a predefined specificity or sensitivity. This method can be advantageous over one that uses a threshold where the patient serves as their own control. In certain examples, by using a population-based threshold, a condition, e.g., high left atrial filling pressure, can be detected with a very high specificity, e.g., 86%, 90%, 100%, etc. Detecting a condition with a high specificity is generally advantageous due to a reduction in false-positives, among other reasons. Conversely, setting or adjusting the threshold to detect a condition with a high specificity typically detects the condition with a lower sensitivity. In the example of FIG. 12, setting or adjusting the threshold to detect a condition with a specificity of 86% detects the condition with a sensitivity of 75%, setting or adjusting the threshold to detect a condition with a specificity of 90% detects the condition with a sensitivity of 71%, and setting or adjusting the threshold to detect a condition with a specificity of 100% detects the condition with a sensitivity of 64%.

In another example, at 1315, if processor 820 determines that the at least one parameter indicative of an atrial filling pressure has not crossed the threshold, then an alert is not generated, and the process flow returns to 1305.

Figure 14:
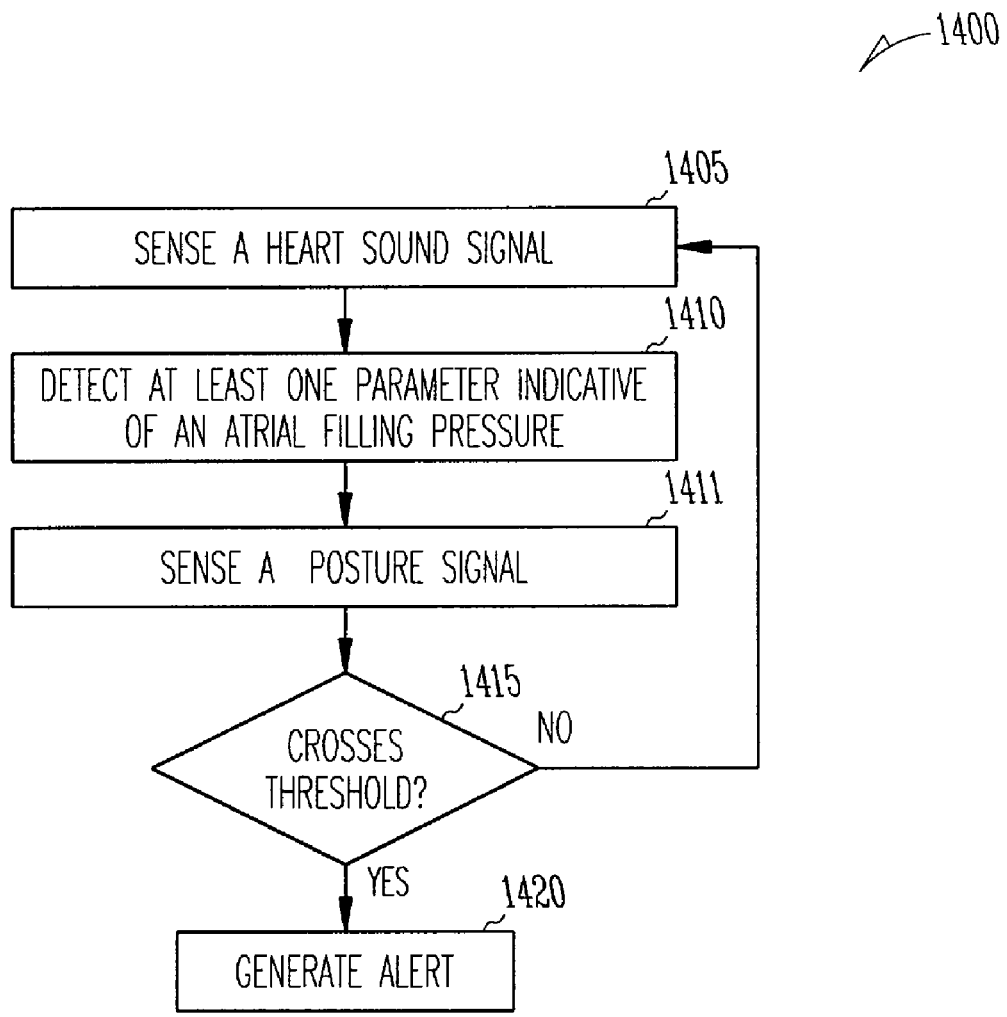
FIG. 14 illustrates generally an embodiment of a method including sensing a heart sound signal, detecting at least one parameter indicative of an atrial filling pressure, sensing a posture signal, and generating an alert when the at least one parameter indicative of an atrial filling pressure crosses a threshold.

FIG. 14 illustrates generally an example of a method 1400 including sensing a heart sound signal, detecting at least one parameter indicative of an atrial filling pressure, sensing a posture signal, and generating an alert when the at least one parameter indicative of an atrial filling pressure crosses a threshold.

At 1405, a heart sound signal is sensed. The heart sound signal can include any signal indicative of a heart sound of a heart. In an example, the heart sound signal can be sensed using the heart sound sensor 810.

At 1410, at least one parameter indicative of an atrial filling pressure is detected. In an example, the at least one parameter indicative of an atrial filling pressure is detected using the heart sound signal. In an example, the at least one parameter indicative of an atrial filling pressure is detected using the heart sound detector 815.

At 1411, a posture signal is sensed. The posture signal can include any signal indicative of a posture or an activity level of a patient. Typically, an atrial filling pressure can be more accurately determined, with a higher sensitivity or with a higher specificity, if the posture or the activity level of the patient is known.

In an example, the threshold can be determined, set, or adjusted using information from the posture signal. Generally, when the patient is lying in the supine, recumbent, prone, or other lying position, or when the patient is inactive or at rest, there exists less noise in the heart sound signal, and thus, a more accurate heart sound signal can typically be sensed. In an example, the threshold can be determined, set, or adjusted using information from the posture signal, e.g., lowering the threshold during long periods of rest, raising the threshold during periods of increased activity, etc.

In another example, the at least one parameter indicative of an atrial filling pressure can be determined or adjusted using information from the posture signal. Generally, heart sound information can be dependent upon patient position. In an example, the heart sound signal or the at least one parameter indicative of an atrial filling pressure can be filtered, adjusted, or attained using information from the posture signal.

At 1415, the method 1400 determines if the at least one parameter indicative of an atrial filling pressure has crossed the threshold. In an example, at 1415, the processor 820 determines if the at least one parameter indicative of an atrial filling pressure has crossed the threshold. In an example, if, at 1415, the at least one parameter indicative of an atrial filling pressure crosses the threshold, then, at 1420, an alert is generated. In another example, the at least one parameter indicative of an atrial filling pressure can be across the threshold for a certain duration (e.g., one or more than one cardiac cycle, one or more than one minute, one or more than one hour, one or more than one day, etc.) before the alert module is configured to generate an alert. In yet another example, the at least one parameter indicative of an atrial filling pressure can cross the threshold for a certain duration (e.g., the at least one parameter crosses the threshold one time per day for 3 consecutive days, the at least one parameter crosses the threshold one time per day for 5 consecutive days, etc.) before the alert module is configured to generate an alert.

In another example, if, at 1415, the at least one parameter indicative of an atrial filling pressure has not crossed the threshold, then an alert is not generated, and the process flow returns to 1405.

Figure 15:
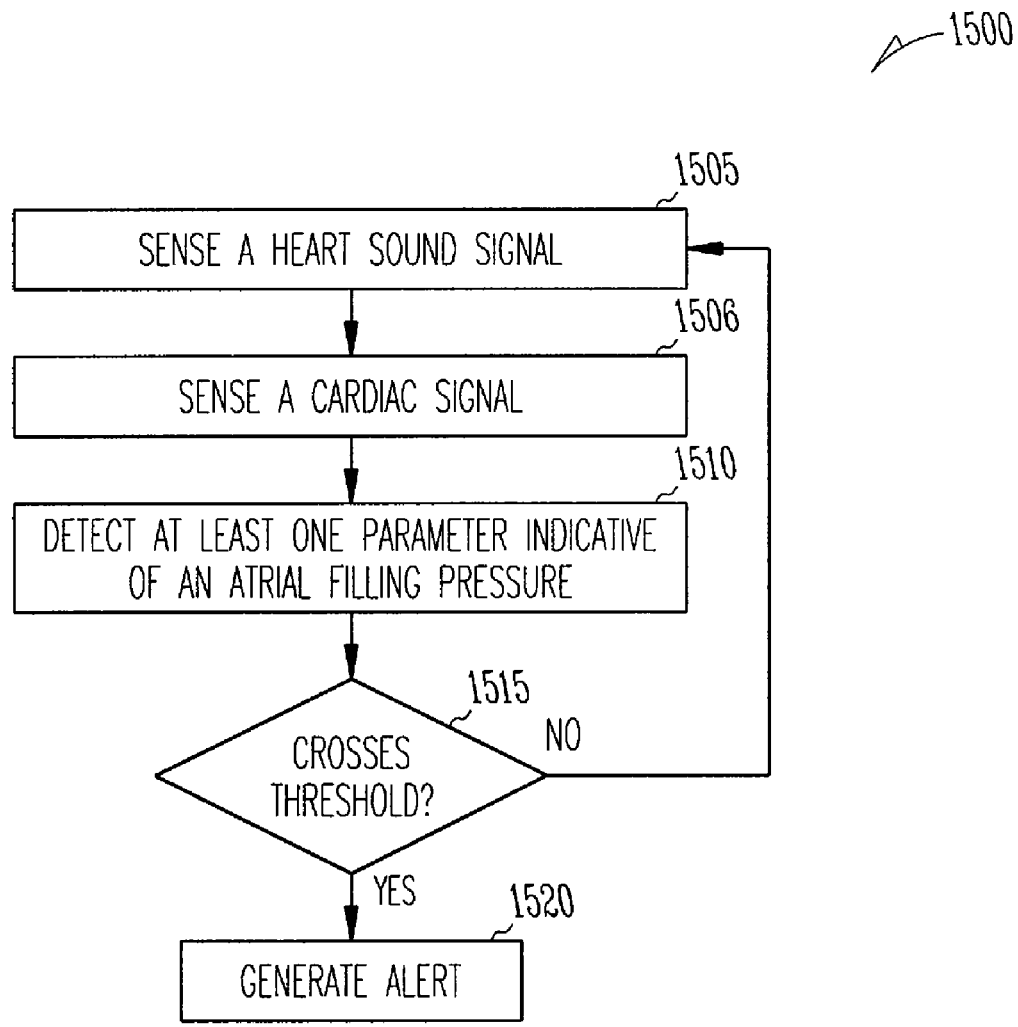
FIG. 15 illustrates generally and embodiment of a method including sensing a heart sound signal, sensing a cardiac signal, detecting at least one parameter indicative of an atrial filling pressure, and generating an alert when the at least one parameter indicative of an atrial filling pressure crosses a threshold.

FIG. 15 illustrates generally an example of a method 1500 including sensing a heart sound signal, sensing a cardiac signal, detecting at least one parameter indicative of an atrial filling pressure, and generating an alert when the at least one parameter indicative of an atrial filling pressure crosses a threshold.

At 1505, a heart sound signal is sensed. The heart sound signal can include any signal indicative of a heart sound of a heart. In an example, the heart sound signal can be sensed using the heart sound sensor 810.

At 1506, a cardiac signal is sensed. The cardiac signal can include any signal indicative of a cardiac signal of the heart. In an example, the cardiac signal can be sensed using the cardiac sensor 825.

At 1510, at least one parameter indicative of an atrial filling pressure is detected. In an example, the at least one parameter indicative of an atrial filling pressure is detected using the heart sound signal and the cardiac signal. In an example, the at least one parameter indicative of an atrial filling pressure is detected using the heart sound detector 815. In another example, the at least one parameter indicative of an atrial filling pressure is detected using the processor 820.

Generally, at 1510, the at least one parameter indicative of an atrial filling pressure includes at least one measurement, feature, characteristic, computation, or interval between at least one cardiac signal feature and at least one heart sound signal feature. Typically, the at least one cardiac signal feature can include at least one feature or component of an ECG signal, e.g., at least one component of a P-wave, at least one component of a Q-wave, at least one component of a R-wave, at least one component of a S-wave, at least one component of a T-wave, or any combination or permutation of features or components of the ECG signal. In certain examples, the at least one measurement, feature, characteristic, computation, or interval between at least one cardiac signal feature and at least one heart sound signal feature includes a systolic time interval (STI) (e.g., a total electromechanical systole (Q-S2), a pre-ejection phase (PEP), a left-ventricular ejection time (LVET), an isovolumetric contraction time (ICT), an interval between S1 and S2 (S1-S2), etc.), a long Q-S1 time interval, a R-S1 time interval, R-S2 interval, etc.

At 1515, the method 1500 determines if the at least one parameter indicative of an atrial filling pressure has crossed the threshold. In an example, at 1515, the processor 820 determines if the at least one parameter indicative of an atrial filling pressure has crossed the threshold. In an example, if, at 1515, the at least one parameter indicative of an atrial filling pressure has crossed the threshold, then, at 1520, an alert is generated. In another example, the at least one parameter indicative of an atrial filling pressure can be across the threshold for a certain duration (e.g., one or more than one cardiac cycle, one or more than one minute, one or more than one hour, one or more than one day, etc.) before the alert module is configured to generate an alert. In yet another example, the at least one parameter indicative of an atrial filling pressure can cross the threshold for a certain duration (e.g., the at least one parameter crosses the threshold one time per day for 3 consecutive days, the at least one parameter crosses the threshold one time per day for 5 consecutive days, etc.) before the alert module is configured to generate an alert.

In another example, if, at 1515, the at least one parameter indicative of an atrial filling pressure has not crossed the threshold, then an alert is not generated, and the process flow returns to 1505.

In other examples, the alert can be generated using a threshold or other methods, including a statistical analysis, a standard deviation, or a constant false alarm-rate technique, such as is described in the co-pending, commonly assigned Siejko et al. U.S. patent application Ser. No. 11/276,735, entitled "PHYSIOLOGICAL EVENT DETECTION SYSTEMS AND METHODS," filed Mar. 13, 2006, which is hereby incorporated by reference in its entirety.

In the examples of FIGS. 8-15, various examples, including sensing a heart sound signal, sensing a posture signal, sensing a cardiac signal, detecting at least one parameter indicative of an atrial filling pressure, determining if the at least one parameter indicative of an atrial filling pressure has crossed a threshold, generating an alert, operating or ceasing to operate a system, activating or deactivating a method, etc., are disclosed. It is to be understood that these examples are not exclusive, and can be implemented either alone or in combination, or in various permutations or combinations.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
an implantable medical device, including:
a heart sound sensor, configured to sense a heart sound signal of a heart;
a heart sound detector, coupled to the heart sound sensor, the heart sound detector configured to detect a second heart sound third heart sound (S2-S3) time interval indicative of an atrial filling pressure of the heart using the heart sound signal; and
a processor, coupled to the heart sound detector, the processor configured to compare the S2-S3 time interval to a threshold.

2. The system of claim 1, wherein the atrial filling pressure includes a left atrial filling pressure.

3. The system of claim 1, wherein the implantable medical device includes a cardiac sensor, coupled to the heart sound detector, the cardiac sensor configured to sense a cardiac signal of the heart; and
wherein the heart sound detector is configured to detect the S2-S3 time interval indicative of an atrial filling pressure of the heart using the heart sound signal and the cardiac signal.

4. The system of claim 1, wherein the processor is configured to compare the S2-S3 time interval to a predefined threshold.

5. The system of claim 1, including a posture sensor, coupled to the processor, the posture sensor configured to sense a posture signal; and
wherein the processor is configured to compare the S2-S3 time interval to the threshold using the posture signal.

6. The system of claim 1, including an alert module, coupled to the processor, the alert module configured to generate an alert using the S2-S3 time interval.

7. The system of claim 6, wherein the alert is configured to be generated with a predefined specificity.

8. The system of claim 7, wherein the alert is configured to be generated with a predefined specificity equal to or greater than 85%.

9. The system of claim 8, wherein the alert is configured to be generated with a predefined specificity equal to or greater than 90%.

10. The system of claim 1, wherein the processor is configured to compare the S2-S3 time interval to a predetermined threshold based on previous S2-S3 time interval information.

11. A method comprising:
sensing a heart sound signal of a heart using an implanted heart sound sensor;
detecting an S2-S3 time interval indicative of an atrial filling pressure of the heart using the heart sound signal; and
comparing the S2-S3 time interval to a threshold.

12. The method of claim 11, wherein detecting the S2-S3 time interval indicative of an atrial filling pressure includes detecting a left atrial filling pressure.

13. The method of claim 11, including:
sensing a cardiac signal of the heart using an implanted cardiac sensor; and
wherein detecting the S2-S3 time interval indicative of an atrial filling pressure of the heart includes using the heart sound signal and the cardiac signal.

14. The method of claim 11, wherein comparing the S2-S3 time interval to a threshold includes comparing the S2-S3 time interval to a predefined threshold.

15. The method of claim 11, including:
sensing a posture signal using a posture sensor; and
wherein comparing the S2-S3 time interval to a threshold includes using the posture signal.

16. The method of claim 11, including generating an alert using the S2-S3 time interval.

17. The method of claim 16, wherein generating an alert includes generating an alert with a predefined specificity.

18. The method of claim 17, wherein generating an alert with a predefined specificity includes generating an alert with a predefined specificity of at least 85%.

19. The method of claim 18, wherein generating an alert with a predefined specificity includes generating an alert with a predefined specificity of at least 90%.

20. The method of claim 11, wherein comparing the S2-S3 time interval to a threshold includes comparing the S2-S3 time interval to a predetermined threshold based on previous S2-S3 time interval information.

* * * * *

UNITED STATES PATENT AND TRADEMARK OFFICE
CERTIFICATE OF CORRECTION

| | | |
|---|---|---|
| PATENT NO. | : 8,048,001 B2 | Page 1 of 1 |
| APPLICATION NO. | : 11/558967 | |
| DATED | : November 1, 2011 | |
| INVENTOR(S) | : Abhilash Patangay et al. | |

It is certified that error appears in the above-identified patent and that said Letters Patent is hereby corrected as shown below:

In column 23, line 50, in Claim 1, delete "sound third" and insert -- sound-third --, therefor.

Signed and Sealed this
Seventh Day of February, 2012

David J. Kappos
*Director of the United States Patent and Trademark Office*